(12) United States Patent
Pezzutto et al.

(10) Patent No.: US 12,365,717 B2
(45) Date of Patent: Jul. 22, 2025

(54) SPECIFIC T CELL RECEPTORS AGAINST EPITOPES OF MUTANT MYD88L265P PROTEIN FOR ADOPTIVE T CELL THERAPY

(71) Applicant: CHARITÉ—UNIVERSITÄTSMEDIZIN BERLIN, Berlin (DE)

(72) Inventors: Antonio Pezzutto, Berlin (DE); Özcan Cinar, Brookline, MA (US)

(73) Assignee: CHARITÉ—UNIVERSITÄTSMEDIZIN BERLIN, Berlin (DE)

( * ) Notice: Subject to any disclaimer, the term of this patent is extended or adjusted under 35 U.S.C. 154(b) by 903 days.

(21) Appl. No.: 17/424,541

(22) PCT Filed: Jan. 21, 2020

(86) PCT No.: PCT/EP2020/051405
§ 371 (c)(1),
(2) Date: Jul. 21, 2021

(87) PCT Pub. No.: WO2020/152161
PCT Pub. Date: Jul. 30, 2020

(65) Prior Publication Data
US 2022/0064257 A1  Mar. 3, 2022

(30) Foreign Application Priority Data
Jan. 21, 2019 (EP) ..................... 19152801

(51) Int. Cl.
| | | |
|---|---|---|
| *C07K 14/725* | (2006.01) |
| *A61K 38/00* | (2006.01) |
| *A61K 40/11* | (2025.01) |
| *A61K 40/32* | (2025.01) |
| *A61K 40/42* | (2025.01) |
| *A61P 35/00* | (2006.01) |
| *C12N 5/0783* | (2010.01) |

(52) U.S. Cl.
CPC .......... *C07K 14/7051* (2013.01); *A61K 40/11* (2025.01); *A61K 40/32* (2025.01); *A61K 40/4201* (2025.01); *A61P 35/00* (2018.01); *C12N 5/0636* (2013.01); *A61K 38/00* (2013.01); *A61K 2239/48* (2023.05)

(58) Field of Classification Search
CPC .............. C07K 14/7051; C07K 14/705; A61K 39/4611; A61K 39/4632; A61K 39/464401; A61K 2239/48; A61K 38/00; A61K 31/7088; A61K 35/00; A61P 35/00; C12N 5/0636; C12N 2510/00
See application file for complete search history.

(56) References Cited

FOREIGN PATENT DOCUMENTS

DE   10 2015 106731 A1   11/2016
WO   WO-2020152161 A1 *   7/2020  ......... A61K 31/7088

OTHER PUBLICATIONS

Poulain et al., Blood, vol. 121, No. 22: 4504-4511, published May 30, 2013.*
Rudolph, M. et. al. "How TCRs Bind MHCs, Peptides, and Coreceptors", 2006 Ann. Rev. Imm. vol. 24:419-446 (Year: 2006).*
Chlewicki et. al."High-affinity, Peptide-specific T Cell Receptors can be Generated by Mutations in the CDR1, CDR2, or CDR3", Journal of Mol. Biol. 2005 pp. 223-239 (Year: 2005).*
Pfeiffer et. al. "In vivo generation of human CD19-CAR T cells results in B-cell depletion and signs of cytokine release syndrome" 2018, EMBO Mol. Med. 10; e9158 p. 1-11 (Year: 2018).*
Blankenstein et al., 2015. Curr Opin Immunol. 33:112-119 (Year: 2015).*
Yu et al., 2018. Cancer Res. 78(10):2457-62 (Year: 2018).*
Knittel et al., 2016. Blood 127(22):2732-2741 (Year: 2016).*
Rovira et al., 2016. Clin Cancer Res 1-10 (Year: 2016).*
Lee et al., 2017. Scientific Reports 7:1785 (Year: 2017).*
International Search Report and Written Opinion dated Feb. 28, 2020, from International Application No. PCT/EP2020/051405, 11 pages.
Nielsen, J.S. et al. "Mapping the human T cell repertoire to recurrent driver mutations in MYD88 and EHZ2 in lymphoma", Oncoimmunology, 2017, vol. 6, No. 7 (10 pages).
Nelde, A. et al. "HLA class I-restricted MYD88 L265P-derived peptides as specific targets for lymphoma immunotherapy", Oncoimmunology, 2017, vol. 6, No. 3 (11 pages).
Weber, A.N. et al. "Oncogenic MYD88 mutations in lymphoma: novel insights and therapeutic possibilities", Cancer Immunology, Immunotherapy (2018) 67:1797-1807.
Danska et al., 1990. J. Exp. Med. 172:27-33.
(Continued)

*Primary Examiner* — Anand U Desai
*Assistant Examiner* — Kathleen Cunningchen
(74) *Attorney, Agent, or Firm* — Meunier Carlin & Curfman LLC

(57) ABSTRACT

Disclosed herein are adoptive T cell therapies or T cell receptor (TCR) gene therapies from the treatment of cancer. The therapies utilize a nucleic acid encoding at least one TCR alpha or beta chain construct of a TCR construct capable of specifically binding to a MYD88 L265P peptide of SEQ ID NO: 2 in the context of HLA-B*07:02 having a high avidity to said peptide/HLA complex. Proteins corresponding to said TCR constructs and host cells, preferably, CD8+ T cells, comprising the TCR constructs are described, as well as the medical use of such nucleic acids, proteins or host cells, in particular, in the diagnosis, prevention and/or treatment of a MyD88 L265P expressing cancer such as a non-Hodgkin B-cell lymphoma selected from the group comprising diffuse large B-cell lymphoma (DLBCL), e.g., activated B-cell-like DLBCL (ABC-DLBCL) or pCNS DLBCL, cutaneous DLBCL, leg-type DLBCL or testicular DLBCL; lymphoplasmacytic lymphoma (LPL), e.g., Waldenström macroglobulinemia (WM); and IgM monoclonal gammopathy (IgM MGUS).

17 Claims, 10 Drawing Sheets
Specification includes a Sequence Listing.

(56) References Cited

OTHER PUBLICATIONS

Garcia et al., 2005. Cell 122(3): 333-336.
Blankenstein et al., 2015. Curr Opin Immunol. 33:112-119.
Yu et al., 2018. Cancer Res. 78(10):2457-62.
Knittel et al., 2016. Blood 127(22):2732-2741.
Rovira et al., 2016. Clin Cancer Res 1-10.
Lee et al., 2017. Scientific Reports 7:1785.
Chervin et al. 2008. J Immunol Methods.339(2):175-84).
Robbins et al., 2008. J Immunol. 180:6116-31.
Linette et al. 2013. Blood 122(6):863-72.
Morgan et al., 2013, J. Immunother. 36, 133-151.
Sommermeyer et al., 2010, J. Immunol. 184, 6223-31.
Legut etal., 2018. Blood 131:311-322.
Eyquem et al., 2017. Nature 543: 113-117.
Roth et al., 2018. Nature 559:405-409.

* cited by examiner

A.

B.

A.

B.

A.

B.

C.

SPECIFIC T CELL RECEPTORS AGAINST EPITOPES OF MUTANT MYD88L265P PROTEIN FOR ADOPTIVE T CELL THERAPY

The present invention is directed to the field of immunotherapy, in particular, adoptive T cell therapy or T cell receptor (TCR) gene therapy of cancer. The invention provides a nucleic acid encoding at least one TCR alpha or beta chain construct of a TCR construct capable of specifically binding to a MYD88 L265P peptide of SEQ ID NO: 2 in the context of HLA-B*07:02 having a high avidity to said peptide/HLA complex. The invention also provides corresponding proteins and host cells, preferably, CD8+ T cells, as well as the medical use of such nucleic acids, proteins or host cells, in particular, in the diagnosis, prevention and/or treatment of a MYD88 L265P mutation bearing cancer such as a non-Hodgkin B-cell lymphoma selected from the group comprising diffuse large B-cell lymphoma (DLBCL), e.g., activated B-cell-like DLBCL (ABC-DLBCL) or Primary CNS DLBCL, cutaneous DLBCL, leg-type DLBCL or testicular DLBCL; lymphoplasmacytic lymphoma (LPL), e.g., Waldenström macroglobulinemia (WM); and IgM monoclonal gammopathy (IgM MGUS).

B-cell derived neoplasms are still among the major causes of death in the western world. Around 1500-2000 new cases of high-grade B-cell lymphoma are expected yearly in Germany. Up to 40% of these patients will relapse after initial standard therapy or will not respond in the first place suggesting the urgent need for alternative treatment options. Lymphoma incidence steeply increases with age, and for many patients aged 75 or more the prognosis is much worse.

Chemotherapy is still the main treatment option for the majority of cancer types despite its limitations regarding toxicity and resistance development. Several chemotherapy regimens in combination with monoclonal antibody Rituximab targeting the CD20 B-cell antigen are widely used as first line treatment for Diffuse Large B-cell Lymphoma, with a cure rate of around 60%. Even high-dose Chemotherapy with stem cell rescue can salvage less than a third of patients with relapsed/refractory disease after first line therapy. Primary CNS lymphoma has an even poorer prognosis: only high-dose chemotherapy appears to be curative, but this is feasible only in a minority of patients because of age limitations and comorbidities, as it occurs at high frequency in patients aged >70 years.

Chimeric antigen receptors (CAR) are chimeras of the antigen-binding domains of antibodies capable of recognizing cell surface antigens combined with TCR domains. T cells engineered to express the CAR thus target cells expressing the antigen to which the CAR binds, irrespective of any HLA restriction.

CAR T cells targeting CD19 have proven successful in around 50% of refractory and relapsed DLBCL patients, demonstrating the potency of adoptive T-cell therapy. Recently, clinical studies of adoptive T-cell therapy (ATT) using chimeric antigenic receptors gene-transfer against the B-cell antigen CD19 has achieved remarkable success and has been designated as "breakthrough cancer therapy". A large majority of researchers are developing this same strategy, mainly by targeting B-cell lineage antigens such as CD19, CD20 and CD22. However, tumor escape by modulation of surface expression of the target antigen is a major limitation of this strategy, leading to relapse in at least 50% of treated patients-despite the high costs. Furthermore, CAR-based ATT can only target cell surface proteins, and not intracellular proteins. Albeit being more specific than chemotherapy, CAR-based ATT is not truly tumor specific, as the whole B-cell compartment, including both malignant and normal B lymphocytes are eliminated after B-cell directed CAR-ATT, frequently leading to severe B-cell depletion that may require long term immunoglobulin substitution.

A TCR is a heterodimeric cell surface protein of the immunoglobulin super-family which is associated with invariant proteins of the CD3 complex involved in mediating signal transduction. TCRs exist in αβ and γδ forms, which are structurally similar, but have quite distinct anatomical locations and probably functions. The alpha and beta chains of native heterodimeric αβTCR are transmembrane proteins, which each comprise two extracellular domains, a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies.

The variable region of each TCR chain comprises variable and joining segments, and in the case of the beta chain also a diversity segment. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. Unique TRAV or TRBV numbers are given to Vα or Vβs by IMGT nomenclature. T cell receptor specificity for the epitopes recognized is mainly determined by the CDR3 regions (Danska et al., 1990. J. Exp. Med. 172:27-33; Garcia et al., 2005. Cell 122 (3): 333-336).

The use of adoptive TCR gene therapy allows equipping the patients' own T cells with desired specificities and generation of sufficient numbers of T cells in a short period of time, avoiding their exhaustion. The TCR may be transduced into all T cells or T-cell subsets such as CD8, central memory T cells or T cells with stem cell characteristics, which may ensure better persistence and function upon transfer. TCR-engineered T cells may be infused into cancer patients that have, e.g., been rendered lymphopenic by chemotherapy or irradiation, inducing homeostatic expansion which greatly enhances engraftment and long term persistence of transferred T cells with higher cure rates.

In contrast to CAR-based strategies, TCR-based adoptive T cell therapy relies on classical TCR recognition of processed epitopes of antigens presented in the context of MHC molecules rather than on antibody recognition as with CARs. This has the advantage that surface expression is not necessary for TCR recognition, and, consequently, modulation of surface antigen expression upon binding of CARs does not pose a limitation. Moreover, cancer mutations occur mostly in intracytoplasmic proteins regulating cell proliferation, survival or sensitivity to drugs and other regulatory signals, and not in surface molecules: T-cell receptors can target any protein independent of cellular localization, greatly widening the spectrum of targetable antigens which can include both lineage specific surface antigens as in case of CARs and truly tumor specific, intracellular antigens.

Ideally, cancer specific mutant antigens, so called "neoantigens", derived by somatic mutations acquired during tumor development, represent the best possible target for immune system recognition since they are strictly expressed by cancer cells, meaning advanced specificity and decreased off-target toxicity. Cancers carrying oncogenic driver mutations are a still very attractive for TCR gene therapy, if the underlying mutations lead to aberrant peptides presented on MHC molecules with high affinity (Blankenstein et al., 2015. Curr Opin Immunol. 33:112-119).

MYD88 is an intracellular adaptor protein. A missense mutation changing leucine in position 265 to proline (L265P) in MYD88 is one of the most common driver mutations which can be found in around one-fifth of all lymphoid malignancies, and even more frequently in aggressive and therapy resistant cases. Said mutation occurs with high frequency in B-cell lymphoma, e.g., in diffuse large B-cell lymphoma (DLBCL), e.g., activated B-cell-like DLBCL (ABC-DLBCL) or Primary CNS DLBCL, cutaneous DLBCL, leg-type DLBCL or testicular DLBCL; lymphoplasmacytic lymphoma (LPL), e.g., IgM monoclonal gammopathy, and in about 90% of Waldenström macroglobulinemia (WM) patients (Yu et al., 2018. Cancer Res. 78 (10): 2457-62; Knittel et al., 2016. Blood 127 (22): 2732-2741; Rovira et al., 2016. Clin Cancer Res 1-10; Lee et al., 2017. Scientific Reports 7:1785).

Use of peptides comprising the MYD88 L265P mutation for cancer immunotherapy has been suggested (DE 10 2015 106 731 A1, Nelde et al., 2017. Oncoimmunology 6 (3): e1219825). Based on in silico predictions, Nelde et al. (2017) identified potential MYD88 L265P containing HLA ligands for several HLA class I restrictions. A set of HLA I MYD88 L265P-derived ligands was shown to elicit specific cytotoxic T cell responses for HLA-B*07 and HLA-B*15, and Nelde et al. discuss if said peptides can be naturally presented.

Nielsen et al. (2017. Oncommunology 6 (7): e1321184) assessed T cells from healthy donors for recognition of common driver mutations, such as the MYD88 L265P mutation, by testing libraries of all possible 8-, 9-, 10- and 11-mer mutant peptides on the donor's T cells. They found CD8+ T cells against the peptide RPIPIKYKA (SEQ ID NO: 1, the bold P represents the L265P mutation) from MYD88 L265P, presented by HLA-B*07:02, in one donor, and found evidence that said peptide can also be processed in human B cells. Other peptides, in particular, a longer peptide RPIPIKYKAM (SEQ ID NO: 2), was also recognized by donor's T cells on target cells pulsed with the peptide, but most T cell lines responding to said peptides failed to recognize B cells transfected with MYD88 L265P. The authors conclude that 75% of their candidate peptides failed to be naturally processed, which would make the TCR recognizing said peptide not suitable for T cell therapy. With regard to the remaining T cell line reactive to the peptide of SEQ ID NO: 1 which could be processed, Nielsen et al. discuss the option of TCR gene therapy, but they suggest that, based on the low number of patients expressing HLA-B*07, the practicality of TCR engineering is limited. T cells are not cloned, and no TCR sequence is provided. The authors thus suggest turning to an expanded list of alternative target antigens that frequently harbor putative driver mutations in lymphoma. Moreover, the authors teach the use of the peptide for therapeutic purpose by vaccination.

In view of this, the present inventors addressed the problem of providing an advantageous TCR construct capable of specifically targeting peptides comprising amino acid substitutions due to driver gene mutations of B-cell lymphomas which can be naturally processed and presented on HLA, wherein, preferably, the TCR construct has a high affinity which allows for therapeutic use of said TCR construct. This problem is solved by the subject matter of the claims.

The inventors provide TCR constructs recognizing epitopes of such antigens in MYD88L265P, namely, TCR constructs binding a MYD88 L265P peptide of SEQ ID NO: 2 in the context of HLA-B*07:02, which TCR have a surprisingly high affinity. In contrast to the teachings of Nielsen et al., they also found that MYD88 L265P can be naturally processed to yield peptides of SEQ ID NO: 2 which are presented in the context of HLA-B*07:02, and T cells targeting said peptide can thus be advantageously used for treatment of tumors expressing MYD88 L265P.

The invention provides a nucleic acid encoding at least one TCR alpha or beta chain construct of a TCR construct capable of specifically binding to a MYD88 L265P peptide of SEQ ID NO: 2 in the context of HLA-B*07:02,
  a) wherein the TCR alpha chain construct comprises a CDR3 sequence of SEQ ID NO: 13, and/or wherein the TCR beta chain construct comprises a CDR3 sequence of SEQ ID NO: 16; or
  b) wherein the TCR alpha chain construct comprises a CDR3 sequence of SEQ ID NO: 23, and/or wherein the TCR beta chain construct comprises a CDR1 sequence having a sequence identity of at least 90% to SEQ ID NO: 24, a CDR2 sequence having a sequence identity of at least 90% to SEQ ID NO: 25 and a CDR3 sequence of SEQ ID NO: 26; or
  c) wherein the TCR alpha chain construct comprises a CDR3 sequence of SEQ ID NO: 33, and/or wherein the TCR beta chain construct comprises a CDR3 sequence of SEQ ID NO: 36; or
  d) wherein the TCR alpha chain construct comprises a CDR3 sequence of SEQ ID NO: 43, and/or wherein the TCR beta chain construct comprises a CDR3 sequence of SEQ ID NO: 46; or
  e) wherein the TCR alpha chain construct comprises a CDR3 sequence of SEQ ID NO: 93,
  and/or wherein the TCR beta chain construct comprises a CDR3 sequence of SEQ ID NO: 96; or
  f) wherein the TCR alpha chain construct comprises a CDR3 sequence of SEQ ID NO: 103, and/or wherein the TCR beta chain construct comprises a CDR3 sequence of SEQ ID NO: 106; or
  g) wherein the TCR alpha chain construct comprises a CDR3 sequence of SEQ ID NO: 113, and/or wherein the TCR beta chain construct comprises a CDR3 sequence of SEQ ID NO: 116; or
  h) wherein the TCR alpha chain construct comprises a CDR3 sequence of SEQ ID NO: 123, and/or wherein the TCR beta chain construct comprises a CDR3 sequence of SEQ ID NO: 126; or
  i) wherein the TCR alpha chain construct comprises a CDR3 sequence of SEQ ID NO: 133,
  and/or wherein the TCR beta chain construct comprises a CDR3 sequence of SEQ ID NO: 136.

As the affinity and specificity may be further optimized by methods known in the art as described in more detail below, the invention also provides a nucleic acid encoding at least one TCR alpha or beta chain construct of a TCR construct capable of specifically binding to a MYD88 L265P peptide of SEQ ID NO: 2 in the context of HLA-B*07:02,
  a) wherein the TCR alpha chain construct comprises a CDR3 sequence having a sequence identity of at least 90% to SEQ ID NO: 13, and/or wherein the TCR beta chain construct comprises a CDR3 sequence having a sequence identity of at least 90% to SEQ ID NO: 16; or
  b) wherein the TCR alpha chain construct comprises a CDR3 sequence having a sequence identity of at least 90% to SEQ ID NO: 23, and/or wherein the TCR beta chain construct comprises a CDR1 sequence having a sequence identity of at least 90% to SEQ ID NO: 24, a CDR2 sequence having a sequence identity of at least 90% to SEQ ID NO: 25 and a CDR3 sequence of at least 90% to SEQ ID NO: 26; or c) wherein the TCR alpha chain construct comprises a CDR3 sequence having a sequence identity of at least 90% to SEQ ID NO: 33, and/or wherein the TCR beta chain construct comprises a CDR3 sequence having a sequence identity of at least 90% to SEQ ID NO: 36; or d) wherein the TCR alpha chain construct comprises a CDR3 sequence having a sequence identity of at least 90% to SEQ ID NO: 43, and/or wherein the TCR beta chain construct comprises a CDR3 sequence having a sequence identity of at least 90% to SEQ ID NO: 46; or e) wherein the TCR alpha chain construct comprises a CDR3 sequence having a sequence identity of at least 90% to SEQ ID NO: 93, and/or wherein the TCR beta chain construct comprises a CDR3 sequence having a sequence identity of at least 90% to SEQ ID NO: 96;

f) wherein the TCR alpha chain construct comprises a CDR3 sequence having a sequence identity of at least 90% to SEQ ID NO: 103, and/or wherein the TCR beta chain construct comprises a CDR3 sequence having a sequence identity of at least 90% to SEQ ID NO: 106; or g) wherein the TCR alpha chain construct comprises a CDR3 sequence having a sequence identity of at least 90% to SEQ ID NO: 113, and/or wherein the TCR beta chain construct comprises a CDR3 sequence having a sequence identity of at least 90% to SEQ ID NO: 116; or h) wherein the TCR alpha chain construct comprises a CDR3 sequence having a sequence identity of at least 90% to SEQ ID NO: 123, and/or wherein the TCR beta chain construct comprises a CDR3 sequence having a sequence identity of at least 90% to SEQ ID NO: 126; or i) wherein the TCR alpha chain construct comprises a CDR3 sequence having a sequence identity of at least 90% to SEQ ID NO: 133, and/or wherein the TCR beta chain construct comprises a CDR3 sequence having a sequence identity of at least 90% to SEQ ID NO: 136.

A preferred TCR construct of which the TCR alpha and/or chain constructs of e) may be part may comprise the variable region(s) of the TCR designated TCR2304.

A preferred TCR construct of which the TCR alpha and/or chain constructs of a) may be part may comprise the variable region(s) of the TCR designated TCR2207.

A preferred TCR construct of which the TCR alpha and/or chain constructs of b) may be part may comprise the variable region(s) of the TCR designated TCR2205. It is noted in the context of the TCR alpha and/or chain constructs of b) that the CDR3 sequence of the beta chain of TCR2205, i.e., SEQ ID NO: 26, has been previously published in an article entitled "Tissue distribution ad clonal diversity of the T and B-cell repertoire in type 1 diabetes in the supplementary data of Seay et al., 2016. JCI Insight. 1 (20): e88242. However, the remaining part of the gene differs, in particular, CDR1 and CDR2, the variant gene subtypes and the corresponding alpha chain sequence are different.

A preferred TCR construct of which the TCR alpha and/or chain constructs of c) may be part may comprise the variable region(s) of the TCR designated TCR1610.

A preferred TCR construct of which the TCR alpha and/or chain constructs of d) may be part may comprise the variable region(s) of the TCR designated TCR1605.

A preferred TCR construct of which the TCR alpha and/or chain constructs of f) may be part may comprise the variable region(s) of the TCR designated TCR2705.

A preferred TCR construct of which the TCR alpha and/or chain constructs of g) may be part may comprise the variable region(s) of the TCR designated TCR2709.

A preferred TCR construct of which the TCR alpha and/or chain constructs of h) may be part may comprise the variable region(s) of the TCR designated TCR2716.

A preferred TCR construct of which the TCR alpha and/or chain constructs of i) may be part may comprise the variable region(s) of the TCR designated TCR2719.

All TCR constructs of the invention are capable of specifically binding to a MYD88 L265P peptide of SEQ ID NO: 2 in the context of HLA-B*07:02. The inventors could show that the histocompatibility antigen HLA-B7:02 can efficiently present this mutation for T-cell receptor recognition, and it is a relatively common MHC haplotype with a frequency of 15-25% in Germany and about 30% among North American Caucasians.

One of the TCR constructs of the invention, wherein the TCR alpha chain construct comprises a CDR3 sequence having a sequence identity of at least 90% to SEQ ID NO: 13, and wherein the TCR beta chain construct comprises a CDR3 sequence having a sequence identity of at least 90% to SEQ ID NO: 16, e.g., TCR2207, is also capable of specifically recognizing a 9-mer, a 11-mer and a 12-mer MYD88 L265P peptide, in particular, a peptide of SEQ ID NO: 1, 3 or 4.

The TCR constructs specifically recognize the peptide of SEQ ID NO: 2, in particular, they do not recognize the corresponding MYD88 wildtype peptide of SEQ ID NO: 3. They also preferably do not have significant cross-reactivity to non-MYD88 L265P self-peptides, in particular, self-peptides presented on the HLA of a patient which is to be treated with the TCR.

The term "capable of specifically binding" or "recognizing" or "specific for" a given antigen, as used herein, means that the TCR construct can specifically bind to and immunologically recognize said epitope and HLA, more preferably with high affinity. For example, a TCR may be considered to have "be able of specifically binding" to the MYD88 L265P peptide of SEQ ID NO: 2 in the context of HLA*B07:02, if T cells expressing the TCR secrete at least about 200 µg/ml or more (e.g. 250 µg/ml or more, 500 µg/ml or more, 750 µg/ml or more, 1000 pg ml or more, 2,000 µg/ml or more, 2,500 µg/ml or more, 5,000 µg/ml or more) of interferon-gamma (IFNγ) upon co-culture with target cells pulsed with a low concentration of the respective peptide (e.g., about $10^{-11}$ M, $10^{-10}$ M, $10^{-9}$ M, $10^{-8}$ M, $10^{-7}$ M, $10^{-6}$ M, $10^{-5}$ M), but not without epitope or with an unrelated control peptide epitope or the wildtype MYD88 peptide of SEQ ID NO: 3. Such "specificity" as described above can—for example—be analyzed with an ELISA.

In the context of the invention, "about" is understood to refer to the defined value +/−10%, preferably, +/−5%.

Affinity (or avidity, because a typical TCR has two binding sites) can be analyzed by methods well known to the skilled person, e.g. by BiaCore, by staining with MHC-peptide multimers and analysing the mean florescence intensity (MFI) on FACS or, preferably, by a non-linear curve analysis of IFNγ response, where affinity inversely correlates with $K_D$ value as shown in example 3 or FIGS. 3A and C herein. A TCR affinity with the $K_D$ value of $10^{-7}$ molar (M) or lower is considered high affinity. Preferably, throughout the invention, the TCR encoded by the TCR construct has an avidity with $K_D$ value of $7.4 \times 10^{-9}$ M or lower to the peptide of SEQ ID NO: 2 in the context of HLA-B*07:02, wherein the avidity more preferably is about $2.4 \times 10^{-9}$ M or lower. Such avidities have been shown be the TCR constructs of the invention with two antigen-binding sites (FIGS. 3A and C).

In one embodiment, in the nucleic acids of the invention, the encoded TCR alpha chain construct comprises a CDR1 sequence having a sequence identity of at least 90% to SEQ ID NO: 91, a CDR2 sequence having a sequence identity of at least 90% to SEQ ID NO: 92 and a CDR3 sequence of SEQ ID NO: 93 and/or the TCR beta chain construct comprises a CDR1 sequence having a sequence identity of at least 90% to SEQ ID NO: 94, a CDR2 sequence having a sequence identity of at least 90% to SEQ ID NO: 95 and a CDR3 sequence of SEQ ID NO: 96.

Preferably, in said nucleic acids of the invention, the TCR alpha chain construct comprises a variable region having a sequence identity of at least 90%, preferably, at least 95% or 100% to SEQ ID NO: 97, and/or the TCR beta chain construct comprises a variable region having a sequence identity of at least 90%, preferably, at least 95% or 100%, to SEQ ID NO: 98. The nucleic acid may comprise SEQ ID NO: 99 and 100 encoding said variable regions, respectively, which represent nucleic acids codon-optimized for expression in human cells.

In one embodiment, in the nucleic acids of the invention, the TCR alpha chain construct comprises a CDR1 sequence having a sequence identity of at least 90% to SEQ ID NO: 11, a CDR2 sequence having a sequence identity of at least 90% to SEQ ID NO: 12 and a CDR3 sequence of SEQ ID NO: 13 and/or the TCR beta chain construct comprises a CDR1 sequence having a sequence identity of at least 90% to SEQ ID NO: 14, a CDR2 sequence having a sequence identity of at least 90% to SEQ ID NO: 15 and a CDR3 sequence of SEQ ID NO: 16.

Preferably, in said nucleic acids of the invention, the TCR alpha chain construct comprises a variable region having a sequence identity of at least 90%, preferably, at least 95% or 100%, to SEQ ID NO: 17, and/or the TCR beta chain construct comprises a variable region having a sequence identity of at least 90%, preferably, at least 95% or 100%, to SEQ ID NO: 18. The nucleic acid may comprise SEQ ID NO: 19 and 20 encoding said variable regions, respectively, which represent codon-optimized nucleic acids.

In one embodiment, in the nucleic acids of the invention, the TCR alpha chain construct comprises a CDR1 sequence having a sequence identity of at least 90% to SEQ ID NO: 21, a CDR2 sequence having a sequence identity of at least 90% to SEQ ID NO: 22 and a CDR3 sequence of SEQ ID NO: 23 and/or the TCR beta chain construct comprises a CDR1 sequence having a sequence identity of at least 90% to SEQ ID NO: 24, a CDR2 sequence having a sequence identity of at least 90% to SEQ ID NO: 25 and a CDR3 sequence of SEQ ID NO: 26.

Preferably, in said nucleic acids of the invention, the TCR alpha chain construct comprises a variable region having a sequence identity of at least 90%, preferably, at least 95% or 100%, to SEQ ID NO: 27, and/or the TCR beta chain construct comprises a variable region having a sequence identity of at least 90%, preferably, at least 95% or 100%, to SEQ ID NO: 28. The nucleic acid may comprise SEQ ID NO: 29 and 30 encoding said variable regions, respectively, which represent codon-optimized nucleic acids.

In one embodiment, in the nucleic acids of the invention, the TCR alpha chain construct comprises a CDR1 sequence having a sequence identity of at least 90% to SEQ ID NO: 31, a CDR2 sequence having a sequence identity of at least 90% to SEQ ID NO: 32 and a CDR3 sequence of SEQ ID NO: 33 and/or the TCR beta chain construct comprises a CDR1 sequence having a sequence identity of at least 90% to SEQ ID NO: 34, a CDR2 sequence having a sequence identity of at least 90% to SEQ ID NO: 35 and a CDR3 sequence of SEQ ID NO: 36.

Preferably, in said nucleic acids of the invention, the TCR alpha chain construct comprises a variable region having a sequence identity of at least 90%, preferably, at least 95% or 100%, to SEQ ID NO: 37, and/or the TCR beta chain construct comprises a variable region having a sequence identity of at least 90%, preferably, at least 95% or 100%, to SEQ ID NO: 38. The nucleic acid may comprise SEQ ID NO: 39 and 40 encoding said variable regions, respectively, which represent codon-optimized nucleic acids.

In one embodiment, in the nucleic acids of the invention, the TCR alpha chain construct comprises a CDR1 sequence having a sequence identity of at least 90% to SEQ ID NO: 41, a CDR2 sequence having a sequence identity of at least 90% to SEQ ID NO: 42 and a CDR3 sequence of SEQ ID NO: 43 and/or the TCR beta chain construct comprises a CDR1 sequence having a sequence identity of at least 90% to SEQ ID NO: 44, a CDR2 sequence having a sequence identity of at least 90% to SEQ ID NO: 45 and a CDR3 sequence of SEQ ID NO: 46.

Preferably, in said nucleic acids of the invention, the TCR alpha chain construct comprises a variable region having a sequence identity of at least 90%, preferably, at least 95% or 100%, to SEQ ID NO: 47, and/or the TCR beta chain construct comprises a variable region having a sequence identity of at least 90%, preferably, at least 95% or 100%, to SEQ ID NO: 48. The nucleic acid may comprise SEQ ID NO: 49 and 50 encoding said variable regions, respectively, which represent codon-optimized nucleic acids.

In one embodiment, in the nucleic acids of the invention, the encoded TCR alpha chain construct comprises a CDR1 sequence having a sequence identity of at least 90% to SEQ ID NO: 101, a CDR2 sequence having a sequence identity of at least 90% to SEQ ID NO: 102 and a CDR3 sequence of SEQ ID NO: 103 and/or the TCR beta chain construct comprises a CDR1 sequence having a sequence identity of at least 90% to SEQ ID NO: 104, a CDR2 sequence having a sequence identity of at least 90% to SEQ ID NO: 105 and a CDR3 sequence of SEQ ID NO: 106.

Preferably, in said nucleic acids of the invention, the TCR alpha chain construct comprises a variable region having a sequence identity of at least 90%, preferably, at least 95% or 100% to SEQ ID NO: 107, and/or the TCR beta chain construct comprises a variable region having a sequence identity of at least 90%, preferably, at least 95% or 100%, to SEQ ID NO: 108. The nucleic acid may comprise SEQ ID NO: 109 and 110 encoding said variable regions, respectively, which represent nucleic acids codon-optimized for expression in human cells.

In one embodiment, in the nucleic acids of the invention, the encoded TCR alpha chain construct comprises a CDR1 sequence having a sequence identity of at least 90% to SEQ ID NO: 111, a CDR2 sequence having a sequence identity of at least 90% to SEQ ID NO: 112 and a CDR3 sequence of SEQ ID NO: 113 and/or the TCR beta chain construct comprises a CDR1 sequence having a sequence identity of at least 90% to SEQ ID NO: 114, a CDR2 sequence having a sequence identity of at least 90% to SEQ ID NO: 115 and a CDR3 sequence of SEQ ID NO: 116.

Preferably, in said nucleic acids of the invention, the TCR alpha chain construct comprises a variable region having a sequence identity of at least 90%, preferably, at least 95% or 100% to SEQ ID NO: 117, and/or the TCR beta chain construct comprises a variable region having a sequence identity of at least 90%, preferably, at least 95% or 100%, to SEQ ID NO: 118. The nucleic acid may comprise SEQ ID NO: 119 and 120 encoding said variable regions, respectively, which represent nucleic acids codon-optimized for expression in human cells.

In one embodiment, in the nucleic acids of the invention, the encoded TCR alpha chain construct comprises a CDR1 sequence having a sequence identity of at least 90% to SEQ ID NO: 121, a CDR2 sequence having a sequence identity of at least 90% to SEQ ID NO: 122 and a CDR3 sequence of SEQ ID NO: 123 and/or the TCR beta chain construct comprises a CDR1 sequence having a sequence identity of at least 90% to SEQ ID NO: 124, a CDR2 sequence having a sequence identity of at least 90% to SEQ ID NO: 125 and a CDR3 sequence of SEQ ID NO: 126.

Preferably, in said nucleic acids of the invention, the TCR alpha chain construct comprises a variable region having a sequence identity of at least 90%, preferably, at least 95% or 100% to SEQ ID NO: 127, and/or the TCR beta chain construct comprises a variable region having a sequence identity of at least 90%, preferably, at least 95% or 100%, to SEQ ID NO: 128. The nucleic acid may comprise SEQ ID NO: 129 and 130 encoding said variable regions, respectively, which represent nucleic acids codon-optimized for expression in human cells.

In one embodiment, in the nucleic acids of the invention, the encoded TCR alpha chain construct comprises a CDR1 sequence having a sequence identity of at least 90% to SEQ ID NO: 131, a CDR2 sequence having a sequence identity of at least 90% to SEQ ID NO: 132 and a CDR3 sequence of SEQ ID NO: 133 and/or the TCR beta chain construct comprises a CDR1 sequence having a sequence identity of at least 90% to SEQ ID NO: 134, a CDR2 sequence having a sequence identity of at least 90% to SEQ ID NO: 135 and a CDR3 sequence of SEQ ID NO: 136.

Preferably, in said nucleic acids of the invention, the TCR alpha chain construct comprises a variable region having a sequence identity of at least 90%, preferably, at least 95% or 100% to SEQ ID NO: 137, and/or the TCR beta chain construct comprises a variable region having a sequence identity of at least 90%, preferably, at least 95% or 100%, to SEQ ID NO: 138. The nucleic acid may comprise SEQ ID NO: 139 and 140 encoding said variable regions, respectively, which represent nucleic acids codon-optimized for expression in human cells.

TCR alpha and/or beta chain constructs may have the characteristics laid out in FIG. 2 for TCR 2304, TCR2207, TCR2205, TCR1610 or TCR1605, or TCR2705, TCR2709, TCR2716 or TCR2719. In one embodiment, the TCR construct of the invention does not comprise a beta chain comprising TRBV28.

Preferably, a nucleic acid of the invention encodes a TCR alpha chain construct and a TCR beta chain construct. In the context of the present invention, "a" is understood to mean "one or more" unless expressly stated otherwise. Accordingly, for example, as the TCR construct of the invention contains both alpha and beta chain constructs, it may be encoded by either one or two nucleic acids. The alpha and beta chain constructs together are capable of specifically binding to the MYD88 L265P peptide in complex with HLA-B*07:02. As intermediate products, the alpha and beta chain constructs or nucleic acids encoding them are also subject matter of the invention by themselves.

Preferably, in all TCR alpha and/or beta chain constructs of the invention, the sequence identity to the CDR regions defined herein is 100%.

However, based on the defined CDR3 and variable region sequences provided by the invention, it is possible to carry out affinity maturation of the TCR sequences (Chervin et al. 2008. J Immunol Methods. 339 (2): 175-84); Robbins et al., 2008. J Immunol. 180:6116-31). Non-synonymous nucleotide substitutions, which lead to amino acid exchanges in the CDR3 sequence, may lead to enhanced affinity of the TCR to target antigen. Furthermore, TCR sequence changes in other parts of the variable TRA and TRB regions may change affinity of the TCR to the peptide-MHC complex. This may increase overall affinity of the TCR to the peptide-MHC, but harbors the risk of unspecific recognition and increased cross-reactivity (Linette et al. 2013. Blood 122 (6): 863-72). It is preferred that TCRs varying from the specific sequences provided retain exclusive specificity for the target antigen provided, i.e., that they are not cross-reactive, most importantly, that they do not have cross-reactivity for human self-peptides. Potential cross-reactivity of TCR can be tested against known self-peptides loaded on cells with the correct MHC allele (Morgan et al., 2013, J. Immunother. 36, 133-151). Accordingly, it is preferred that adoptive transfer of T cells expressing the TCR construct of the invention has no negative effects on healthy tissue.

A TCR alpha and/or beta chain construct of the invention may comprise all characteristics or domains corresponding to its native counterpart, but this is not essential. Preferably, the TCR alpha and/or beta chain construct comprises at least a variable region, or a variable and a constant region, e.g., the variable and/or constant region having at least 60%, at least 70%, at least 80%, at least 90% or at least 95% sequence identity to a human variable or constant TCR region. For adoptive TCR therapy, it is preferred that the TCR construct comprises full length TCR alpha and beta chains comprising variable, constant and transmembrane regions. The TCR construct preferably is of essentially or exclusively human origin to minimize immunogenicity. Human TCR alpha and beta constant regions are e.g. shown in SEQ ID NO: 7 (alpha) and SEQ ID NO: 10 (beta, TCRBC2, alternatively, TCRRBC1 may also be used). To prevent pairing with endogenous TCR chains, the constructs of the invention however preferably contain one or more, e.g., 1-5, 1-10 or 1-20, amino acid exchanges, insertions or deletions in comparison to a human sequence, e.g., providing an additional cysteine to enable formation of an additional disulfide bond (Sommermeyer et al., 2010, J. Immunol. 184, 6223-31). The constant regions of such TCR may be minimally "murinized", by substituting a few AA (usually 9) of the human constant region sequence with the murine sequence (e.g., SEQ ID NO: 6 (alpha) and SEQ ID NO: 9 (beta)). The constant region of the TCR alpha and beta chain construct may also be a murine constant region (SEQ ID NO: 5 (alpha) and SEQ ID NO: 8 (beta, TCRBC2, alternatively, TCRRBC1 may also be used)). Both alpha and beta chain constant regions are of the same type, e.g., both may be minimally murinized.

The construct may also be a chimeric antigen receptor, or part of it, wherein, e.g. a human TCR variable region may be linked to a different immunoglobulin constant domain, e.g. an IgG constant domain, or to an antibody domain capable of specifically binding to an antigen such as CD3 T-cell antigen.

Single chain constructs (scTCR) are encompassed as well as heterodimeric TCR constructs. An scTCR can comprise a variable region of a first TCR chain construct (e.g., an alpha chain) and an entire (full-length) second TCR chain (e.g., a beta chain), or vice versa. Furthermore, the scTCR can optionally comprise one or more linkers which join the two or more polypeptides together. The linker can be, for instance, a peptide which joins together two single chains, as described herein. Also provided is such a scTCR of the invention, fused to a cytokine, e.g., a human cytokine, such as IL-2, IL-7 or IL-15.

The TCR construct according to the invention can also be provided in the form of a multimeric complex, comprising at least two scTCR molecules, wherein said scTCR molecules are each fused to at least one biotin moiety, and wherein said scTCRs are interconnected by biotin-strepavidin interaction to allow the formation of said multimeric complex. Also provided are multimeric complexes of a higher order, comprising more than two, e.g., four, scTCR of the invention.

The TCR construct of the invention can be modified to comprise a detectable label, such as, for instance, a radio-isotope, a fluorophore (e.g., fluorescein isothiocyanate (FITC), phycoerythrin (PE)), an enzyme (e.g., alkaline phosphatase, horseradish peroxidase), and particles (e.g., gold particles or magnetic particles).

The nucleic acid of the invention, in particular if it encodes at least one TCR alpha and beta chain construct of the TCR construct, may be, e.g., a vector allowing for expression of the encoded protein in a host cell, e.g., a human T cell, such as a viral vector, a transposon or a vector suitable for CRISPR/CAS based recombination (Legut et al., 2018. Blood 131:311-322; Eyquem et al., 2017. Nature 543:113-117; Roth et al., 2018. Nature 559:405-409). In one embodiment, the vector allows for integration into the host genome.

Preferably, the TCR alpha chain construct and/or TCR beta chain construct or TCR construct of the invention is a vector. Suitable vectors include those designed for propagation and expansion, or for expression or both, such as plasmids and viruses. The vector may be an expression vector suitable for expression is a host cell selected from the group comprising a human T cell or a human T cell precursor, preferably, a human T cell such as CD8+ T cell, e.g., a CD8+ central-memory T cell, CD8+ effector-memory T cell, CD8+ stem cell-like T cell. The vector may be a viral vector, e.g. a retroviral, in particular gamma-retroviral or lentiviral vector. Examples of suitable expression vectors include the retroviral vector MP71. The recombinant expression vector comprises regulatory sequences, such as transcription and translation initiation and termination codons, regulatory untranslated region, inter ribosomal entry sites, which are specific to the type of host cell (for example, bacterium, fungus, plant, or animal cell, e.g., a human CD8+ T cell as defined above) into which the vector is to be introduced and in which the expression of the nucleic acid of the invention shall be performed. Furthermore, the vector of the invention may include one or more marker genes, which allow for selection of transformed or transfected hosts. The recombinant expression vector can comprise a native or, preferably, heterologous promoter operably linked to the nucleotide sequence encoding the construct of the invention, or to the nucleotide sequence which is complementary to or which hybridizes to the nucleotide sequence encoding the constructs of the invention. The selection of promoters includes, e.g., strong, weak, inducible, tissue-specific and developmental-specific promoters. The promoter can be a non-viral promoter or a viral promoter. Preferably, it is a heterologous promoter, i.e., a promoter not naturally linked to TCR in human T cells, such as long terminal repeat promoter, which is suitable for expression in human T cells. The inventive recombinant expression vectors can be designed for either transient expression, for stable expression, or for both. Also, the recombinant expression vectors can be made for constitutive expression or for inducible expression.

The present invention also provides a protein, i.e., an alpha or beta chain construct, or, preferably, a TCR receptor construct comprising both alpha and beta chain constructs, which is capable of specifically binding HLA-*B07:02 in combination with the epitope of SEQ ID NO: 2. The protein is preferably encoded by the nucleic acids of the invention. It is preferably expressed as a transmembrane protein by a host cell.

The invention also provides a host cell comprising a nucleic acid or protein of the invention. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell or T cell precursor, in particular, a human T cell. The T cell can be any T cell, such as a cultured T cell, e.g. a primary T cell, or a T cell from a cultured T cell line, or a T cell obtained from a mammal, preferably, it is a T cell or T cell precursor from a human patient, in particular, from the human patient who is to be treated. The T cell of autologous or allogeneic origin can be obtained from numerous sources, such as blood, bone marrow, lymph node, the thymus, or other tissues or fluids. T cells can also be enriched for or purified. Preferably, the T cell is a human T cell. More preferably, the T cell is a T cell isolated from a human, e.g., a human patient. The T cell can be any type of T cell, but it preferably is a CD8+ cell. It can be of any developmental stage, including but not limited to tumor infiltrating cells (TILs), effector cells, central effector cells, memory T cells, naive T cells, and the like, preferably central-memory T cells.

The host cell of the invention preferably comprises a nucleic acid of the invention and/or a protein of the invention, wherein the host cell preferably is a CD8+ T cell, optionally, a human CD8+ T cell.

The invention also provides a pharmaceutical composition comprising
  a) a nucleic acid of the invention encoding a TCR construct capable of specifically binding to a MYD88 L265P peptide of SEQ ID NO: 2 in the context of HLA-B*07:02; or
  b) a protein of the invention comprising a TCR construct capable of specifically binding to a MYD88 L265P peptide of SEQ ID NO: 2 in the context of HLA-B*07:02; or
  c) a host cell of the invention expressing a TCR construct capable of specifically binding to a MYD88 L265P peptide comprising SEQ ID NO: 2 in the context of HLA-B*07:02.

Preferably, the pharmaceutical composition comprises a human CD8+ host cell of the invention, as defined herein. Said host cell may, e.g., comprise a vector encoding a TCR construct comprising a TCR alpha chain construct and a TCR beta chain construct capable of specifically recognizing the peptide of SEQ ID NO: 2 in the context of HLA-B*07:02. Preferably, the vector is an expression vector for expression of both alpha and beta chain constructs on one nucleic acid, e.g., separated by a p2A element. The variable regions of the TCR chains as defined herein, e.g., of TCR2304, TCR2207, TCR2205, TCR1610 or TCR1605, preferably, TCR2304, are linked with constant regions, preferably, with minimally murinized constant regions.

Alternatively, the patient may also be administered a nucleic acid of the invention, in particularly, an expression vector, for in vivo transduction of T cells.

The pharmaceutical composition may also be part of a kit comprising further therapeutics, e.g., an antibody such as rituximab, an immunotoxin (such as inotuzumab ozogamicin), or a radioimmunoconjugate), or a CAR, which may target a B-cell lineage antigen (for example CD19, CD20, CD22 or CD79), preferably, a CAR capable of targeting CD19, a small molecule such as a kinase inhibitor or a chemotherapeutic agent, including combination chemotherapy and even high dose chemotherapy. The pharmaceutical composition may be for use in combination with any of the above further therapeutics, administered prior to, or concomitantly with or after the pharmaceutical composition. The pharmaceutical composition of the invention may also be combined in one composition or in a kit with an agent capable of inducing IFNγ expression in the target tumor cells to enhance processing of the peptide of SEQ ID NO: 2.

The pharmaceutical composition of the invention or the kit of the invention may be for use in the diagnosis, prevention and/or treatment of a disease, in particular in a patient suspected of comprising cells expressing a MYD88 protein with a L265P mutation. The disease preferably is a tumor disease, e.g. a benign or malignant tumor disease. In a preferred embodiment, the tumor cells have been confirmed to express MYD88 L265P and/or HLA-B*07:02, in particular, both.

Preferably, the patient has a non-Hodgkin B-cell lymphoma selected from the group comprising:
  diffuse large B-cell lymphoma (DLBCL), preferably, activated B-cell-like DLBCL (ABC-type DLBCL) or Primary CNS lymphoma, cutaneous DLBCL, leg-type DLBCL or testicular DLBCL;
  lymphoplasmacytic lymphoma (LPL), preferably, Waldenström macroglobulinemia (WM); and
  IgM monoclonal gammopathy (IgM MGUS).

Preferably, the disease is treated. Reduction of the risk of getting a disease is also considered prevention of a disease, wherein, preferably, the risk of the treated subject is reduced below the normal level in a comparative population, preferably, the risk is reduced by at least 10%, at least 25%, at least 50% or at least 75%, or 100%.

The present invention also provides a method for treating a subject suffering from a disease as specified above, in particular, a tumor or tumor disease comprising administering a nucleic acid, protein or host cell of the invention. Preferably the subject is a subject in need of such a treatment, i.e. a patient. The subject in preferred embodiments is a mammalian subject, preferably a human patient, suffering from a tumor or tumor disease. The active agent is administered in an effective amount.

One preferred medicinal use of the invention relates to immune therapy, preferably adoptive T cell therapy. The product and methods of the invention are particularly useful in the context of adoptive T cell therapy. The administration of the compounds of the invention can for example involve the administration, e.g., infusion of T cells of the invention into said patient. Preferably such T cells are autologous T cells of the patient which have been genetically modified to express the TCR of the present invention, e.g., which were in vitro transduced with a nucleic acid of the present invention.

The treatment of the invention may be first-line treatment of the patient. Preferably, it is second-line treatment of the patient, e.g., if the patient has relapsed or is refractory to therapy with one or more alternative agents (e.g., small molecule inhibitors, chemotherapy, antibody or CAR-based therapy, for example against a B-cell lineage antigen such as CD19).

Protein TCR constructs of the invention may also, e.g., be used for diagnostic purposes to find out if a subject expresses MYD88 L265P, and, in particular, if the epitope according to SEQ ID NO: 2 is presented by HLA*B07:02. To this end, such constructs are preferably labelled to facilitate detection. Preferably, a patient found to present said epitope on HLA*B07:02 is treated by an adoptive T cell therapy of the invention, or alternatively, a TCR gene therapy of the invention.

The invention also provides a method of testing if a human subject, e.g., a B-cell lymphoma patient, expresses MYD88 L265P, comprising contacting a sample obtained from the subject comprising tumor cells, e.g., derived from the subject's blood, with a (preferably labelled) TCR construct of the invention, or with a host cell of the invention expressing a TCR construct of the invention. Said method may further comprise detecting the label, e.g., by FACS or microscopic methods, or detecting activation of said T cells, which can be FACS based. Detecting activation of said T cells may comprise detection of T cell activation markers such as CD137 (and, optionally, expression of the TCR construct of the invention) e.g., by FACS, detecting expression of cytokines, e.g., by ELISA, ELISPOT or PCR-based methods.

The method may also comprise steps of informing the subject of the expression or lack of expression of MYD88 L265P, and optionally, if the patient expresses MYD88 L265P, treatment of a subject who is a patient with a pharmaceutical composition of the invention.

Of course, presence or absence of MYD88 L265P can also be determined in other ways, e.g., by sequencing, PCR-based methods or antibody-based methods.

The invention also relates to a method of preparing a host cell of the invention, comprising introducing an expression vector encoding a TCR construct of the invention into a suitable host cell, preferably, a human CD8+ T cell isolated from a patient. Said host cell can then be reintroduced into the patient The present invention is further illustrated in the following examples with reference to the accompanying figures and sequences, nevertheless, without being limited thereto. For the purposes of the present invention, all references as cited herein are incorporated by reference in their entirety.

Figure Legends:

FIG. 1: Generation of Mutation Specific Tcells

A. Schematic explanation of methodology for generation of mutation-specific T cells. B. Representative streptamer staining from clone-10 (TCR1610) after a single re-stimulation. C. Bulk T-cell clones were tested for selective reactivity against mutant peptide by co-culturing with peptide loaded autologous PBMCs overnight before the FACS isolation of streptamer-positive cells. Response was measured by IFNγ ELISA.

FIG. 2: Identification of Mutation-Specific T-Cell Receptors (TCRs)

Representative construct of TCR gene cassettes.

FIG. 3: Analysis of TCR Avidity

A./C. Non-linear curve analysis of IFNγ response by TCR-transduced CD8+ T cells from healthy donors when co-cultured with K562 cells, that were transduced with HLA*B07:02 and loaded with different concentrations of mutant peptide (SEQ ID NO: 2). Response to mutant peptide was detectable down to the concentration of $10^{-4}$ μg/ml with $K_D$ values within the nano molar (high-affinity) range. B./D. IFNγ response to corresponding wild type (WT) peptide (SEQ ID NO: 6). Mutation-specific TCRs show more than 10000-fold higher affinity to the mutant peptide.

FIG. 4: Mutation-Specific Activation of TCR-Engineered T Cells

A. Mutation-specific activation of TCR2207-transduced T cells against K562 cells with or without HLA-B7 expression, also virally transduced to express complete length wild type or mutant (L265P) MYD88, shown by flow cytometry analysis after 16 hours co-culture. B./C. Comparative mutation specific activation analysis of TCR-transduced T cells. IFNγ response measured by ELISA shows mutation-specific and HLA-B7-restricted response. The epitope can be processed and presented by human cells.

FIG. 5: Mutation-Specific Cytotoxicity of TCR-Engineered T Cells

A. Viability of HLA-B7-positive target cells that were co-cultured for 16 hours with T cells expressing the TCRs of the invention (shown: the 3 highest avidity TCRs), analyzed by flow cytometry. Cells were gated on GFP-positive as reporter of wild type or mutant MYD88 expression, and viability was analyzed by intracellular staining of activated-Caspase-3 (a-Caspase-3) in combination with a fixable dead cell stain. The number of viable cells is provided in the lower left quadrant. B./C. Viability of target cells for comparative cytotoxicity analysis of T cells transduced with different TCRs. Target cells that express the mutation and HLA*B07:02 were specifically killed by TCR-transduced T cells. Strength of cytotoxicity strongly correlated with TCR affinity.

FIG. 6: Mutation-Specific Activation of TCR-Engineered T Cells Against Lymphoma Cell Lines A. Flow cytometric activation analysis of T cells transduced with one of the 2 highest avidity TCRs, after 16-h co-culture with OCI-Ly3 (ABC-like DLBCL, homozygous MYD88-L265P) and HBL-1 (ABC-like DLBCL, heterozygous MYD88-L265P) lymphoma cell lines. Since both cell lines were negative for HLA-B7, they were virally transduced to express it (shown as: "Cell line_B7"). OCI-Ly3 cells transduced with HLA-B7 were strongly recognized by TCR-engineered T cells. Weaker response was observed against heterozygous mutant HBL-1 cells, which was slightly improved when target cells were pre-treated overnight with 50 ng/ml human IFNγ prior to co-culture, which is known to improve proteasomal processing of peptides and MHC presentation. B. Mutation-specific and HLA-B7-restricted activation of T cells transduced with TCR2304.

FIG. 7: Mutation-Specific Cytotoxicity Against Lymphoma Cell Lines

A. Flow cytometric viability analysis (as explained in FIG. 5) of OCI-Ly3 lymphoma cells after 16 h co-culture with TCR2304-transduced T cells. B. Mutation-specific killing by TCR2304-transduced T cells. C. Antigen induced proliferation of TCR2304-transduced T cells following 72-h co-culture with HLA-B7-positive OCI-Ly3 cells. T cells were labelled with CSFE to trace proliferation prior to co-culture.

FIG. 8: Characterization of Peptide-MHC Binding Behavior of TCRs Via Alanine-Scan A. An alanine scan was performed by exchanging every amino acid in the mutant epitope (SEQ ID NO: 2) one by one with Alanine to investigate the impact of single amino acids on the peptide-MHC-TCR relation. All peptides were separately loaded on HLA-B7 expressing K562 cells and co-cultured with TCR-transduced T cells for 16 hours to measure IFNγ production by ELISA. B. Amino acid positions affecting IFNγ response more than 50% are considered important for peptide-MHC-TCR relation, and this binding motif is used for off-target cross-reactivity prediction using an online tool called Expitope (Jaravine et al. 2017). Peptides with predicted HLA-B7 binding (SEQ ID NO: 141-152) from this analysis for TCR2304, were again loaded on HLA-B7 expressing K562 cells and co-cultured for 16 hours with TCR-transduced T cells from 3 different donors. No cross-reactivity was observed against any of these peptides.

FIG. 9:

A. Activation analysis of TCR2304-transduced T cells via IFNγ ELISA, after 16-h co-culture with SU-DHL-6 (GBC-like DLBCL, wild-type MYD88) OCI-Ly3 (ABC-like DLBCL, homozygous MYD88-L265P) and TMD8 (ABC-like DLBCL, heterozygous MYD88-L265P) lymphoma cell lines. Since all cell lines were negative for HLA-B7, they were virally transduced to express it (shown as: "Cell line_B7"). OCI-Ly3 and TMD8 cells transduced with HLA-B7 were strongly recognized by TCR-engineered T cells. B. Flow cytometric viability analysis (as explained in FIG. 5) of lymphoma cells after 16 h co-culture with TCR2304-transduced T cells showing mutation-specific killing.

EXAMPLES

Example 1: Generation of Mutation Specific T Cells

PBMCs were isolated from HLA-B7-positive healthy donors' blood. Monocytes were separated by plastic adherence for generation of dendritic cells (DC) and following 3 days of culture with 800 IU/ml GM-CSF and 10 ng/ml IL-4 in RPMI with 1% human serum, immature dendritic cells (imDC) were cultured overnight with addition of 10 ng/ml LPS and 50 ng/ml Interferon gamma (IFNγ) for maturation. Mature dendritic cells (mDC) were then loaded with mutant peptide (RPIPIKYKAM, SEQ ID NO: 2)) and used for priming autologous CD8-positive naïve T cells ($5 \times 10^5$ T cells/well in 48-well culture plates, in donor-dependently varying DC-T cell ratio). After 10 days, cells from each well were stained with a custom streptamer (HLA*B07:02-RPIP-IKYKAM), or stained for T cell activation markers such as CD137 (4-1BB) following a short (~6 hours) peptide re-stimulation. Positively stained wells were re-stimulated with peptide-loaded autologous PBMCs for expansion, in the case it was necessary to obtain enough cells for FACS isolation.

A schematic explanation of the methodology for generation of mutation-specific T cells is shown in FIG. 1A. FIG. 1B shows a representative streptamer staining from clone-10 (TCR1610) after a single re-stimulation.

Bulk T-cell clones were tested for selective reactivity against mutant peptide by co-culturing with peptide loaded autologous PBMCs overnight before the FACS isolation of streptamer-positive or peptide-reactive cells. Response was measured by IFNγ ELISA (FIG. 1C).

Example 2: Identification of Mutation-Specific T-Cell Receptors (TCR)

After final testing with an IFNγ ELISA, viable CD8 and streptamer-positive cells were isolated separately from each reactive T-cell clone by FACS. Total RNA isolation was performed. TCR alpha and beta genes were amplified via 5'-RACE PCR and cloned. Multiple bacterial clones from each TCR-chain were sequenced for analysis of T-cell clonality. Table 1 shows CDR3, the SEQ ID Nos thereof and gene subtypes of MyD88-L265P mutation-specific TCRs and Table 2 shows a list of CDR1, and CDR2 amino acid sequences.

TABLE 1

| TCR | Chain | SEQ ID NO | CDR3 | V-gene | J-gene | D-gene |
|---|---|---|---|---|---|---|
| 1336 | α | 73 | CAASGRYDYKLSF | TRAV13-1*02 | TRAJ20*01 | — |
|  | β | 76 | CATASDLQGDRSTEAFF | TRBV15*02 | TRBJ1-1*01 | TRBD1*01 |
| 1605 | α | 43 | CAEGTGSARQLTF | TRAV13-2*01 | TRAJ22*01 | — |
|  | β | 46 | CASGPFRDSVLTLVANVLTF | TRBV28*01 | TRBJ2-6*01 | TRBD2*01 |
| 1610 | α | 33 | CAPLGGGYNKLIF | TRAV21*01 | TRAJ4*01 | — |
|  | β | 36 | CASRLPTTDEKLFF | TRBV6-6*02 | TRBJ1-4*01 | TRBD1*01 |
| 2202 | α | 53 | CLSLSDSNYQLIW | TRAV4*01 | TRAJ33*01 | — |
|  | β | 56 | CASSVGQGSYEQYF | TRBV9*01 | TRBJ2-7*01 | TRBD1*01 |
| 2205 | α | 23 | CLVGRDGGSYIPTF | TRAV4*01 | TRAJ6*01 | — |
|  | β | 26 | CASSAGQGAYEQYF | TRBV9*02 | TRBJ2-7*01 | TRBD1*01 |
| 2207 | α | 13 | CAVDVGYSTLTF | TRAV1-2*01 | TRAJ11*01 | — |
|  | β | 16 | CSARDRSGTLGGELFF | TRBV20-1*01 | TRBJ2-2*01 | TRBD2*02 |
| 2211 | α | 83 | CIVRVMKTSYDKVIF | TRAV26-1*01 | TRAJ50*01 | — |
|  | β | 86 | CASSEPRTSGISYNEQFF | TRBV10-1*02 | TRBJ2-1*01 | TRBD2*02 |
| 2219 | α | 63 | CGTAHLRAGSYQLTF | TRAV30*01/ TRAV30*02 | TRAJ28*01 | — |
|  | β | 66 | CASSSSSGGAFNEQFF | TRBV27*01 | TRBJ2-1*01 | TRBD2*01 |
| 2304 | α | 93 | CAVRASGTYKYIF | TRAV1-2*01 | TRAJ40*01 | — |
|  | β | 96 | CASQDSYEQYF | TRBV12-3*01 | TRBJ2-7*01 | No result |
| 2705 | α | 103 | CAMSGTGGFKTIF | TRAV12-3*01 | TRAJ9*01 | — |
|  | β | 106 | CASSQDRPNYYGYTF | TRBV4-3*01 | TRBJ1-2*01 | TRBD1*01 |
| 2709 | α | 113 | CILRDRYGGSQGNLIF | TRAV26-2*01 | TRAJ42*01 | — |
|  | β | 116 | CASSYWPTTGESTDTQYF | TRBV6-2*01/ TRBV6-3*01 | TRBJ2-3*01 | TRBD1*01 |
| 2716 | α | 123 | CAFMKPYSGGGADGLTF | TRAV38-1*01 | TRAJ45*01 | — |
|  | β | 126 | CASSLAGTTVYNEQFF | TRBV13*01 | TRBJ2-1*01 | TRBD2*01 |
| 2719 | α | 133 | CLVGADSNYQLIW | TRAV4*01 | TRAJ33*01 | — |
|  | β | 136 | CASSPGGGAYEQYF | TRBV9*01 | TRBJ2-7*01 | TRBD2*01 |

TABLE 2

| TCR | Chain | SEQ ID NO (CDR1) | CDR1 | SEQ ID NO (CDR2) | CDR2 |
|---|---|---|---|---|---|
| 1336 | α | 71 | DSASNY | 72 | IRSNVGE |
|  | β | 74 | LNHNV | 75 | YYDKDF |
| 1605 | α | 41 | NSASDY | 42 | IRSNMDK |
|  | β | 44 | MDHEN | 45 | SYDVKM |
| 1610 | α | 31 | DSAIYN | 32 | IQSSQRE |
|  | β | 34 | MNHNY | 35 | SVGAGI |
| 2202 | α | 51 | NIATNDY | 52 | GYETK |
|  | β | 54 | SGDLS | 55 | YYNGEE |
| 2205 | α | 21 | NIATNDY | 22 | GYKTK |
|  | β | 24 | SGDLS | 25 | YYNGEE |
| 2207 | α | 11 | TSGFNG | 12 | NVLDGL |
|  | β | 14 | DFQATT | 15 | SNEGSKA |
| 2211 | α | 81 | TISGNEY | 82 | GLKNN |
|  | β | 84 | WNHNN | 85 | SYGVHD |
| 2219 | α | 61 | KALYS | 62 | LLKGGEQ |
|  | β | 64 | MNHEY | 65 | SMNVEV |
| 2304 | α | 91 | TSGFNG | 92 | NVLDGL |
|  | β | 94 | SGHNS | 95 | FNNNVP |
| 2705 | α | 101 | NSAFQY | 102 | TYSSGN |
|  | β | 104 | LGHNA | 105 | YSLEER |

TABLE 2-continued

| TCR | Chain | SEQ ID NO (CDR1) | CDR1 | SEQ ID NO (CDR2) | CDR2 |
|---|---|---|---|---|---|
| 2709 | α | 111 | TISGTDY | 112 | GLTSN |
|  | β | 114 | MNHEY | 115 | SVGEGT |
| 2716 | α | 121 | TSENNYY | 122 | QEAYKQQN |
|  | β | 124 | PRHDT | 125 | FYEKMQ |
| 2719 | α | 131 | NIATNDY | 132 | GYKTK |
|  | β | 134 | SGDLS | 135 | YYNGEE |

The identified variable domains were combined with murine constant domain sequences for experimental characterization of TCRs, and synthesized with codon-optimization for expression in human cells. TCR gene cassettes encoding the TRBV in combination with a murine TRBC and the TRAV in combination with a murine TRAC, separated by a p2A signal, were constructed as described in detail in Obenaus et al. 2015 and Sommermeyer et al. 2010 (cf. FIG. 2).

Example 3: Analysis of TCR Avidity

Peripheral CD8+ T cells from HLA-B7 positive healthy donors were successfully transduced to express mutation specific TCRs, with no signs of fratricide, and co-cultured with K562 cells that were transduced with HLA*B07:02 and loaded with different concentrations of mutant peptide. The IFNγ response was determined by ELISA. FIG. 3A/C show the non-linear curve analysis of IFNγ response by TCR-engineered T cells against the titration of mutant peptide. A response to mutant peptide was detectable down to the concentration of $10^{-4}$ µg/ml with $K_D$ values within the nano molar (high-affinity) range. FIG. 3B/D show a non-linear curve analysis of IFNγ response to the corresponding wild type peptide titration. Mutation-specific TCRs shown more than 10000-fold higher affinity to the mutant peptide. Table 3 shows the avidities of the different TCRs analyzed.

TABLE 3

TCR affinity (shown as $K_D$) to SEQ ID NO: 2 in the context of HLA-B*07:02.

| TCR | $K_D$ (µg/ml) | $K_D$ (M)* |
|---|---|---|
| 2207 | 0.003 | $2.4 \times 10^{-9}$ |
| 2304 | 0.003 | $2.4 \times 10^{-9}$ |
| 2205 | 0.004 | $3.2 \times 10^{-9}$ |
| 1605 | 0.009 | $7.4 \times 10^{-9}$ |
| 1610 | 0.009 | $7.4 \times 10^{-9}$ |
| 2202 | 0.033 | $2.7 \times 10^{-8}$ |
| 2219 | 0.123 | $1 \times 10^{-7}$ |
| 1336 | 0.387 | $3.1 \times 10^{-7}$ |
| 2211 | 0.560 | $4.6 \times 10^{-7}$ |
| 2705 | 0.020 | $1.6 \times 10^{-8}$ |
| 2709 | 0.102 | $8.3 \times 10^{-8}$ |
| 2716 | 0.099 | $8.1 \times 10^{-8}$ |
| 2719 | 0.024 | $1.9 \times 10^{-8}$ |

*Molecular weight of peptide SEQ ID NO: 2 is 1216.54 g/mol.

TCR2304 and TCR2207 show the highest avidity against mutant peptide with the KD of 0.003 µg/ml, which equals to 2.4 nM, for SEQ ID NO:2.

Example 4: Mutation-Specific Activation of TCR-Engineered T Cells

K562 cells with or without HLA-B7 were virally transduced to express complete length wild type or mutant (L265P) MYD88-coupled to the expression marker GFP via p2A and used as artificial target cells for evaluation of cytotoxic reactivity of TCR-engineered T cells. When co-cultured for 16 hours, six of the TCRs led to recognition of target cells expressing the mutant MyD88 without prior peptide loading, suggesting that the epitope can successfully be processed and presented by human cells.

FIG. 4A shows the mutation specific activation of T cells transduced with one of the TCRs, TCR2207, by flow cytometry analysis staining the activation marker CD137. FIG. 4B/C show a comparative mutation specific IFNγ response by T cells transduced with different TCRs measured by ELISA, showing a mutation-specific and HLA-B7-restricted response.

Example 5: Mutation Specific Cytotoxicity of TCR-Transduced T Cells

TCR-transduced T cells were co-cultured with K562 cells that express full length wild type or mutant MYD88 linked with p2A to GFP as an expression marker under the control of the same promoter with or without HLA-B7 for 16 hours. Target cells that express mutation and HLA*B07:02 were specifically killed by TCR-transduced T cells. FIG. 5A shows viability of HLA-B7-positive target cells that were co-cultured for 16 hours with T cells expressing one of the 3 highest avidity TCRs, analyzed by flow cytometry. Cells were gated on GFP-positive as reporter of wild type or mutant MYD88 expression, and viability was analyzed by intracellular staining of activated-Caspase-3 (a-Caspase-3) in combination with a fixable dead cell stain. FIG. 5B/C show viability of target cells for comparative cytotoxicity analysis of T cells transduced with different TCRs.

Example 6: Mutation-Specific Activation of TCR-Engineered T Cells Against Lymphoma Cell Lines In order to investigate their functional potential against mutation in a more natural-like expression level, activation of T cells transduced with one of the 2 highest avidity TCRs was analyzed by flow cytometry after 16-h co-culture with OCI-Ly3 (ABC-like DLBCL, homozygous MYD88-L265P) or HBL-1 (ABC-like DLBCL, heterozygous MYD88-L265P) lymphoma cell lines. Since both cell lines were negative for HLA-B7, they were virally transduced to express it (shown as: "Cell line_B7"). OCI-Ly3 cells transduced with HLA-B7 were strongly recognized by TCR-engineered T cells. Weaker response was observed against heterozygous mutant HBL-1 cells, which was slightly improved when target cells were pre-treated overnight with 50 ng/ml human IFNγ prior to co-culture. IFNγ is known to improve proteasomal processing of peptides and MHC presentation in some cases.

FIG. 6A shows a flow cytometry analysis of T-cell response against OCI-Ly3 and HBL-1 cells. FIG. 6B shows mutation-specific and HLA-B7-restricted activation of T cells transduced with TCR2304 against OCI-Ly3 cells.

Example 7: Mutation-Specific Cytotoxicity Against Lymphoma Cell Lines

T cells transduced with TCR2304 were labelled with CSFE and co-cultured with OCI-Ly3 cells with or without HLA-B7. Viability of target lymphoma cells was analyzed as explained previously in Example 5.

FIG. 7A shows viability of OCI-Ly3 cells with or without HLA-B7 expression after 16-h co-culture with TCR2304-transduced T cells. FIG. 7B shows mutation-specific lymphoma cell-killing by TCR2304-transduced T cells. FIG. 7C shows antigen induced proliferation of TCR2304-transduced T cells following 72-h co-culture with HLA-B7-positive OCI-Ly3 cells, as decreasing fluorescence intensity of CSFE indicates cell division only in TCR-transduced cells.

Example 8: Characterization of Peptide-MHC Binding Behavior of TCRs Via Alanine-Scan A list of peptides was created by exchanging every amino acid in the mutant epitope (SEQ ID NO: 2) one by one with Alanine to investigate the impact of single amino acids to the peptide-MHC-TCR relation. All these peptides were separately loaded on HLA-B7 expressing K562 cells and co-cultured with TCR-transduced T cells for 16 hours. Different number and group of amino acids were observed to be essential for recognition by different TCRs (binding motif). Nevertheless, the proline in the position 2, which reflects the amino acids substitution L265P on mutant MyD88, was absolutely necessary for all TCRs, demonstrating the specificity of TCRs to the mutation (FIG. 8A). The possibility of cross-reactivity that might be caused by binding-sequence similarity to other human proteins is analyzed individually for TCRs using an online tool called Expitope (Jaravine et al. 2017) as a part of safety screening. In the case of TCR2304, this analysis has revealed 12 peptides in human proteome with binding motif similarity (up to 5 mismatch positions) and varying affinity prediction to HLA-B7 (SEQ ID NO: 141-152). All these peptides were again loaded on HLA-B7 expressing K562 cells for a co-culture with TCR-transduced T cells from 3 different donors. No TCR recognition was observed against any of the peptides (FIG. 8B).

Example 9

For a better understanding of TCR recognition and T cell function against cells harboring MyD88 L265P mutation naturally, TCR2304-transduced T cells from 3 different healthy donors were co-cultured for 16-hours with DLBCL cell lines; SU-DHL-6 (wild-type MYD88), OCI-Ly3 (homozygous MYD88 L265P) or TMD8 (heterozygous MYD88 L265P) with or without HLA-B7 expression.

SEQUENCE LISTING

Figure 1:
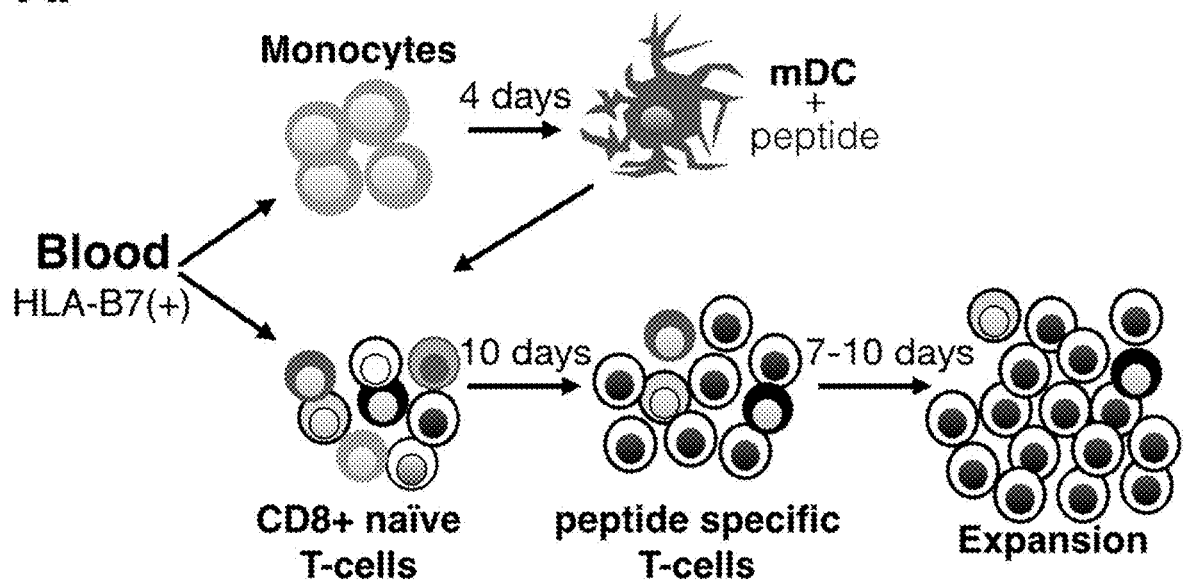
Figure 1:
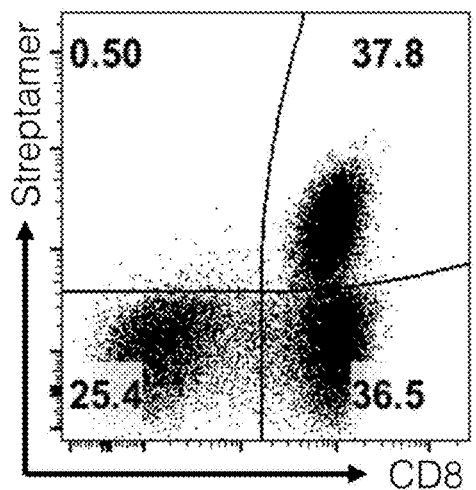
Figure 1:
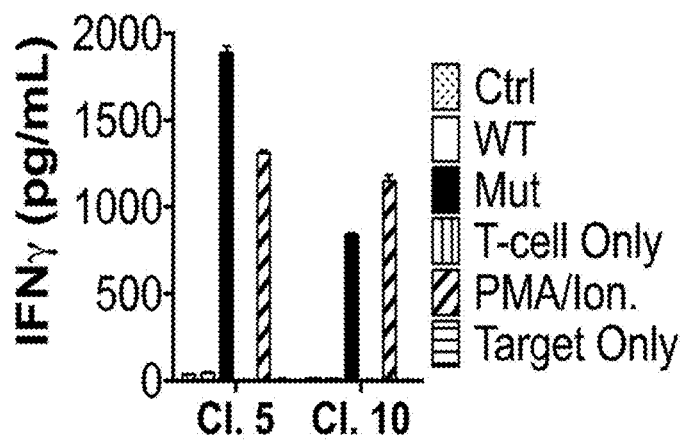
Figure 2:
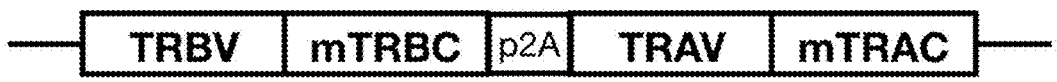
Figure 3:
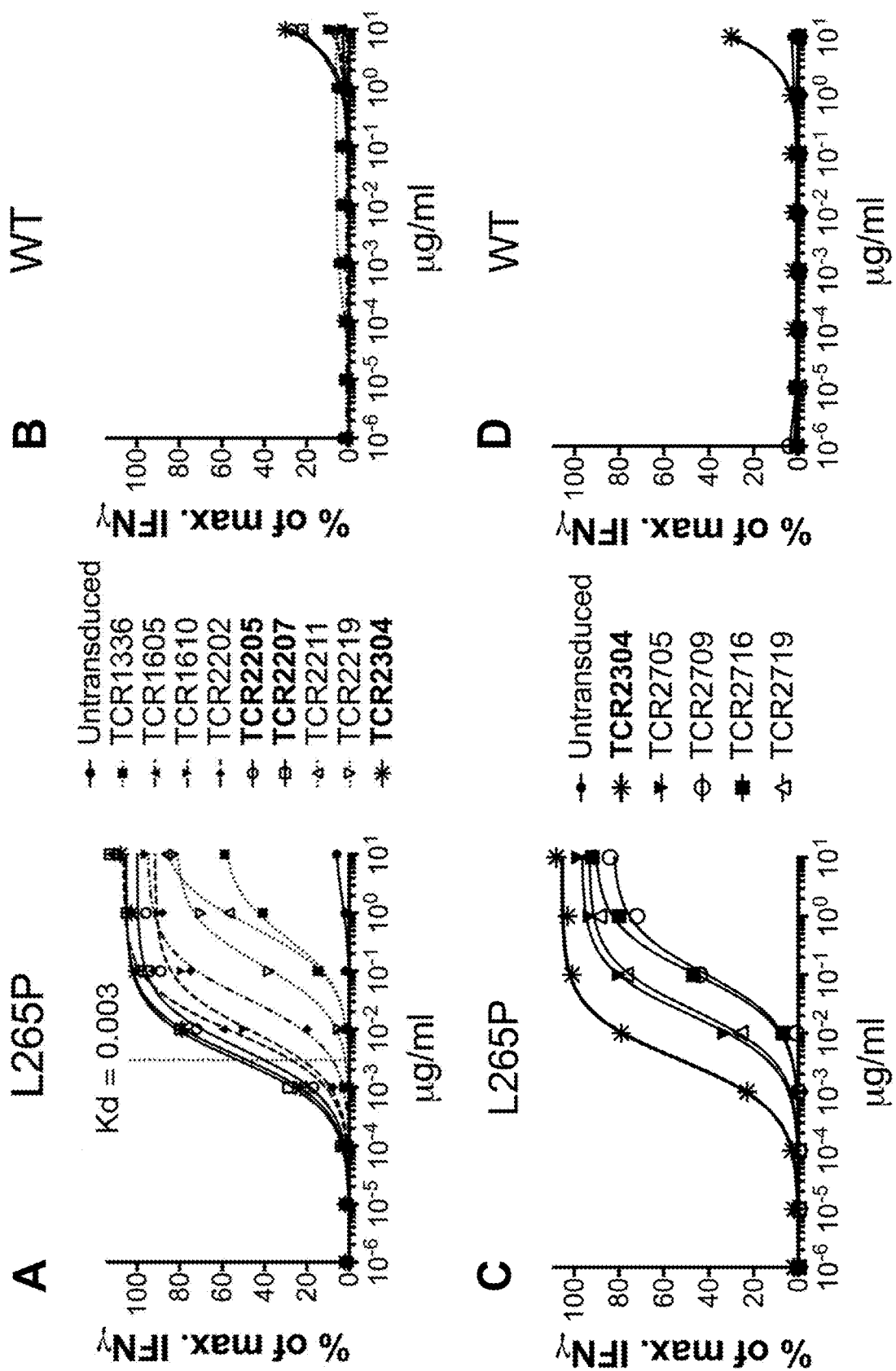
Figure 4:
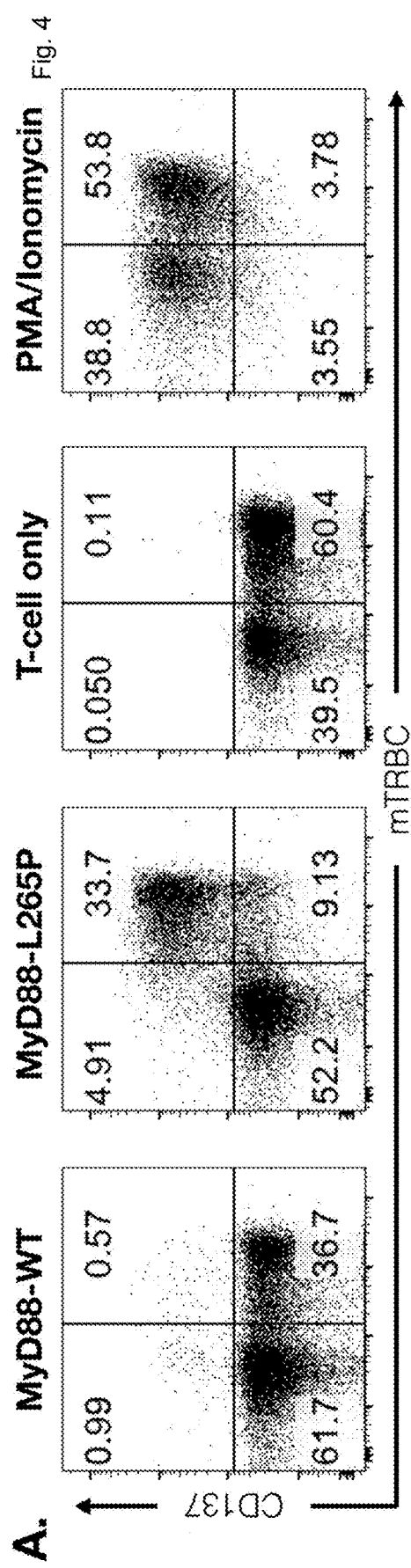
Figure 4:
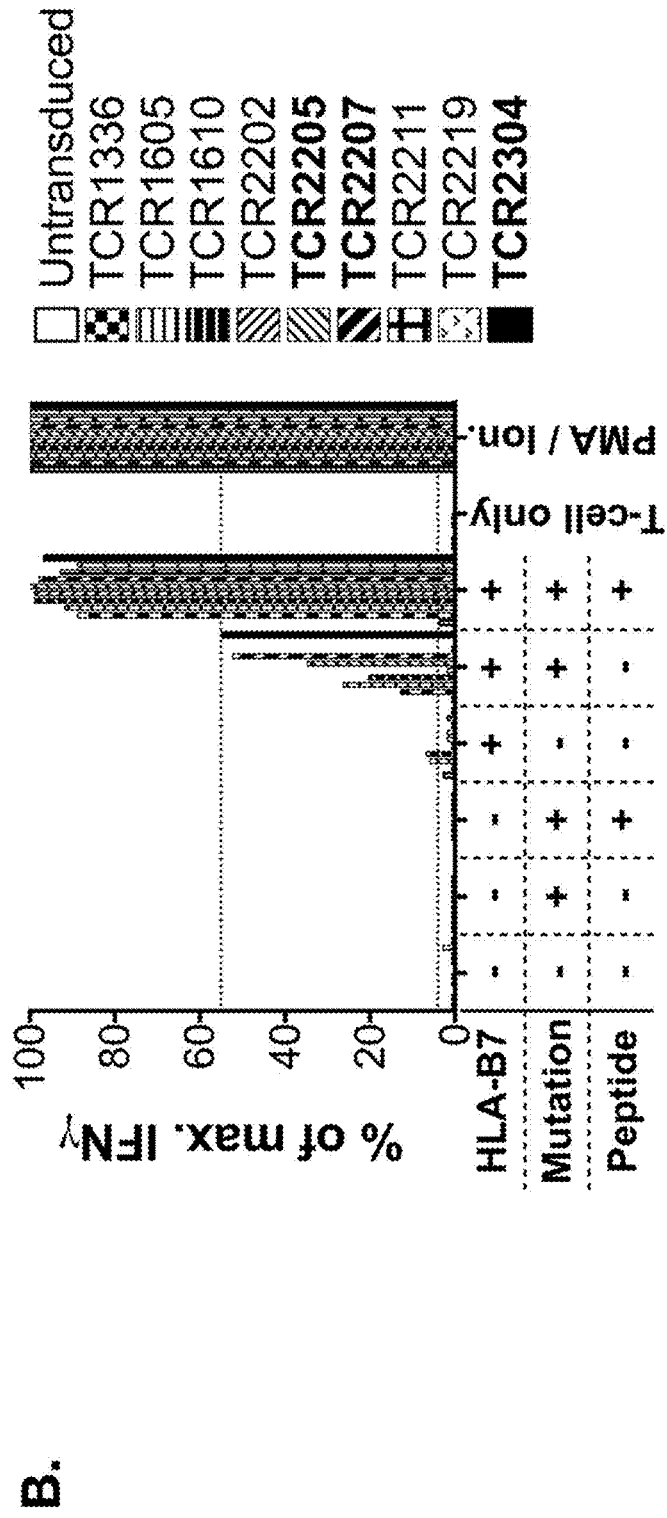
Figure 4:
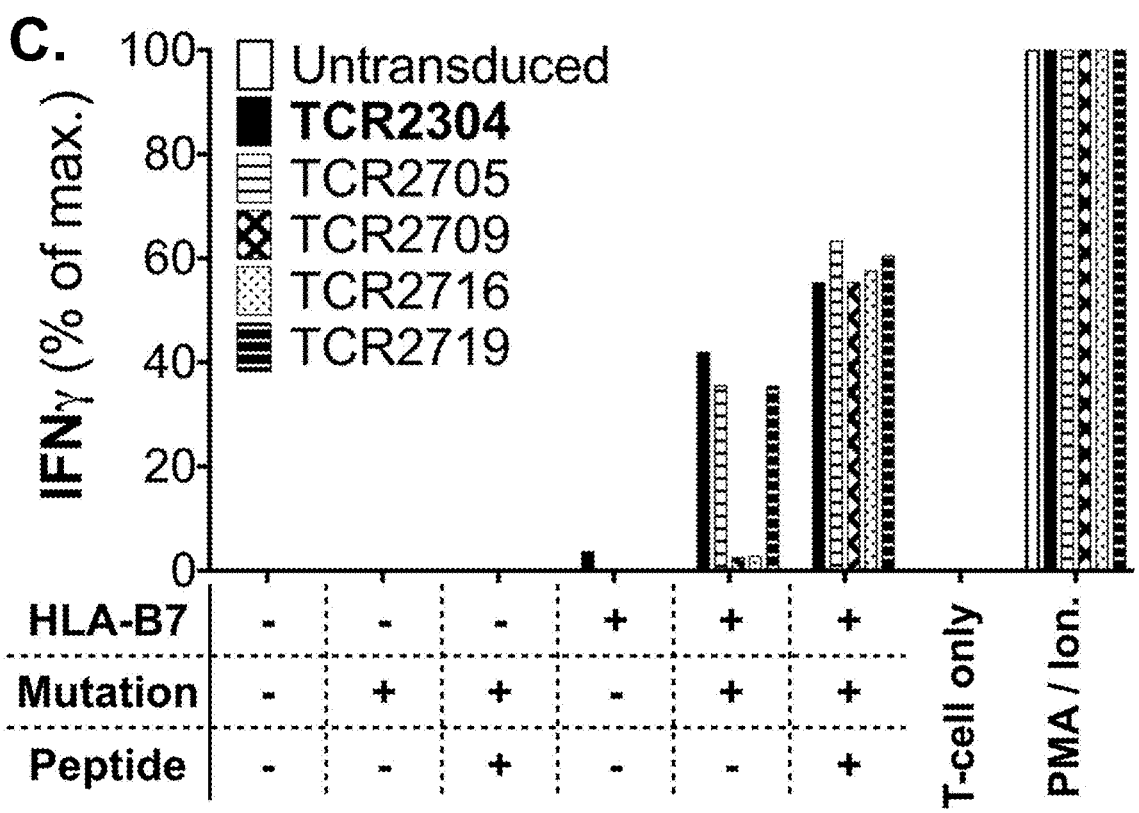
Figure 5:
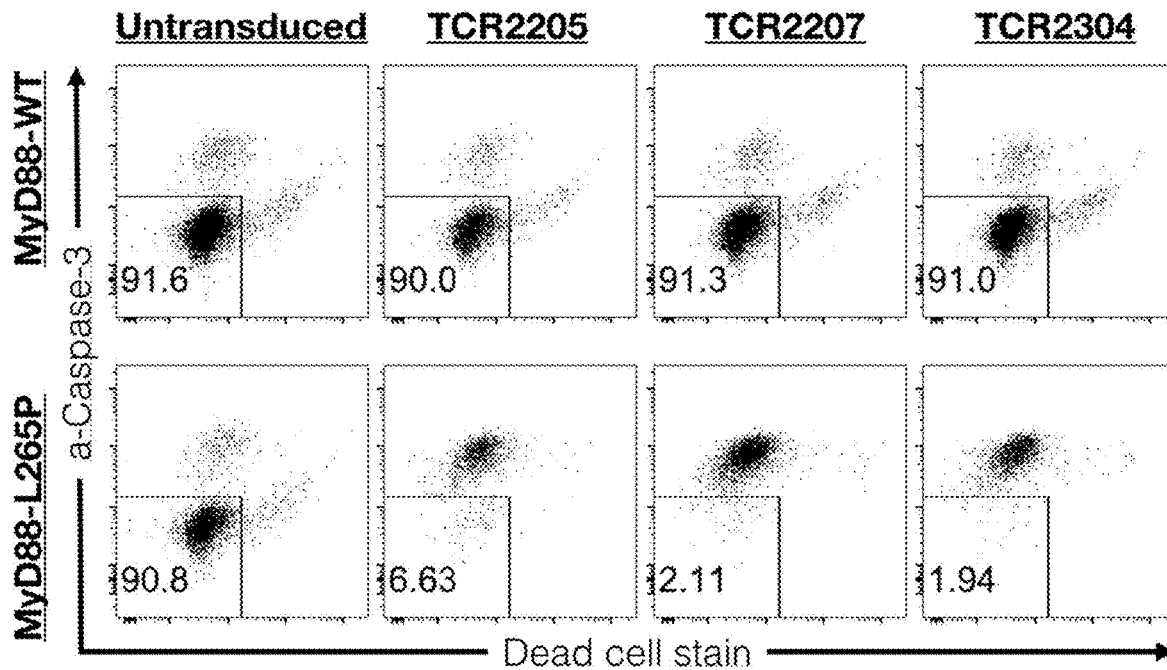
Figure 5:
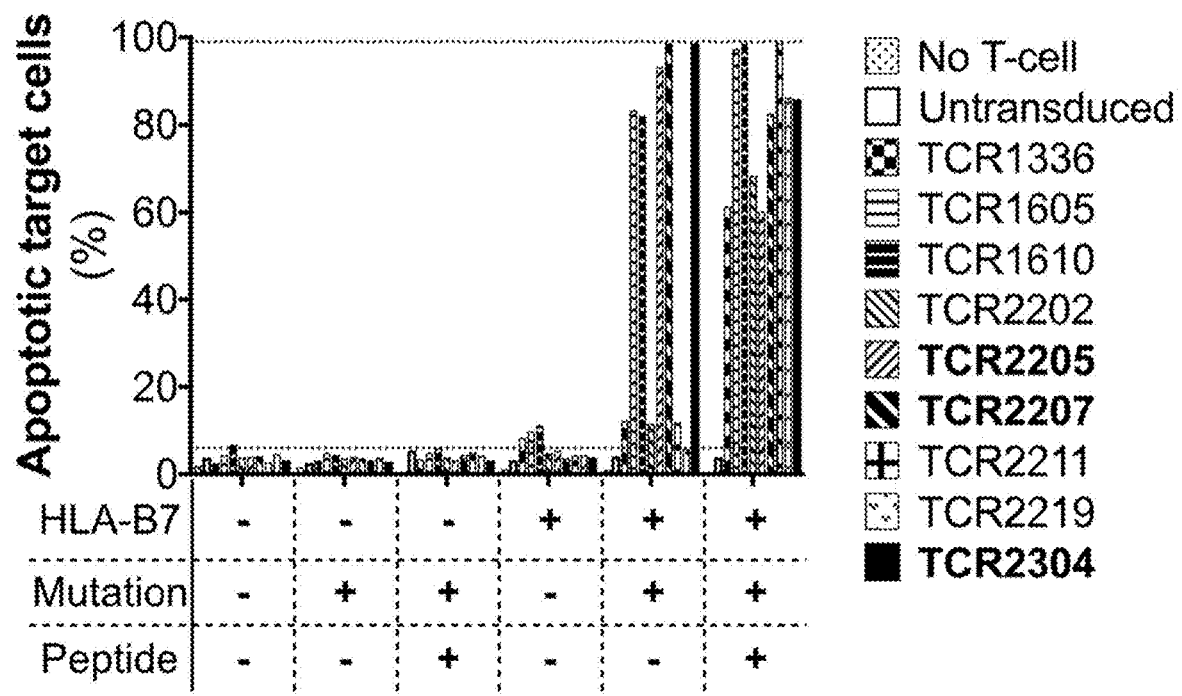
Figure 5:
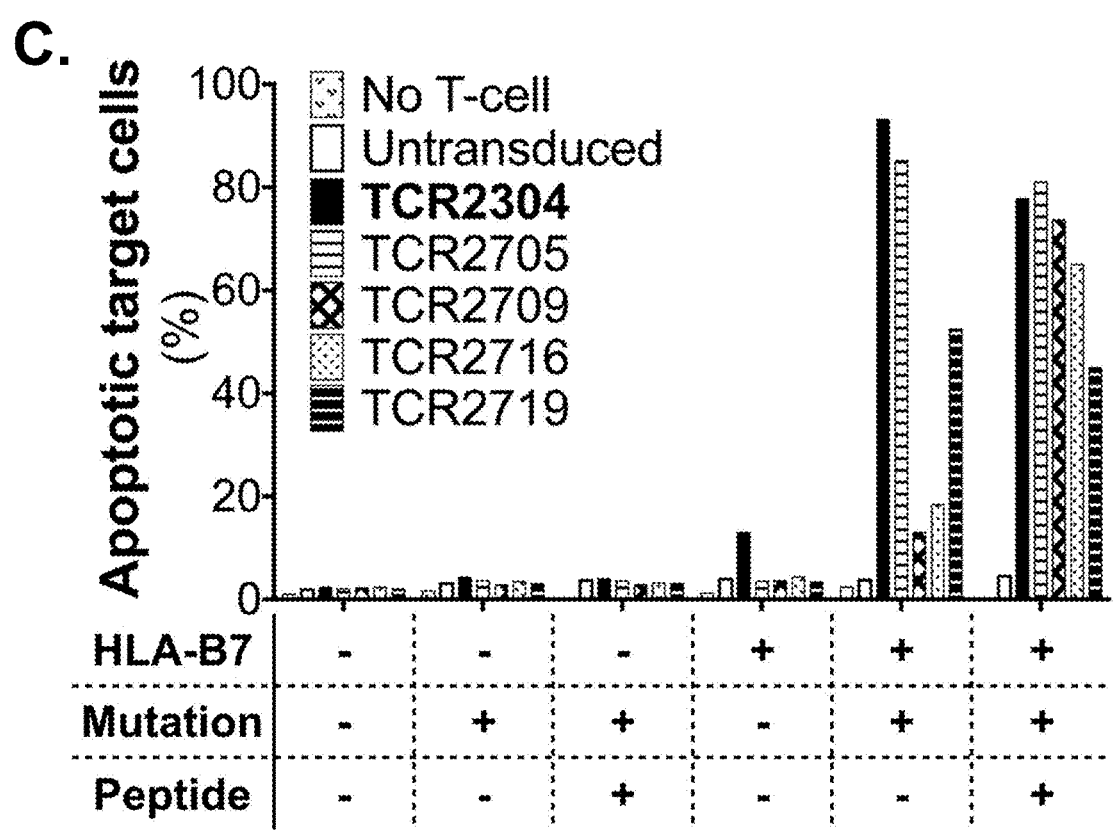
Figure 6:
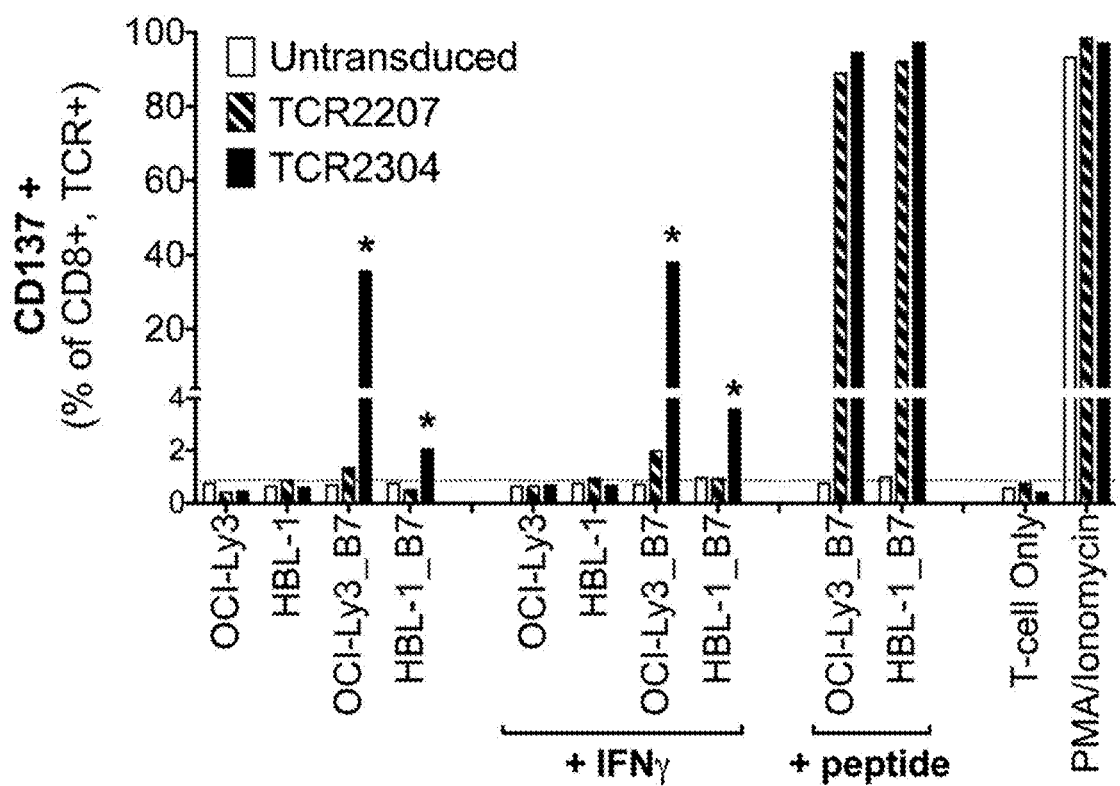
Figure 6:
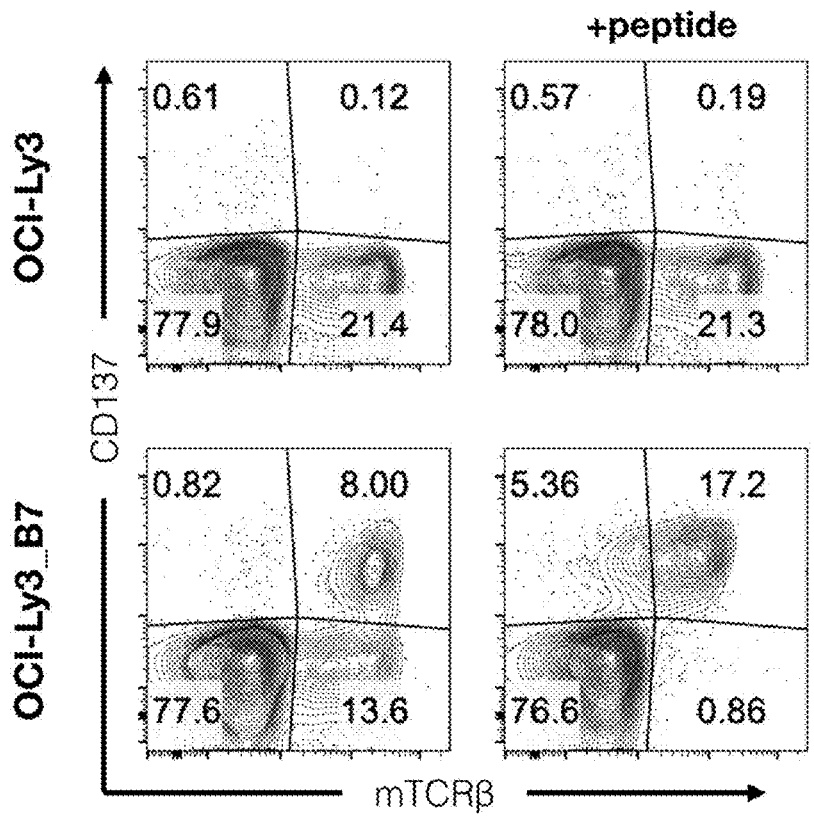
Figure 7:
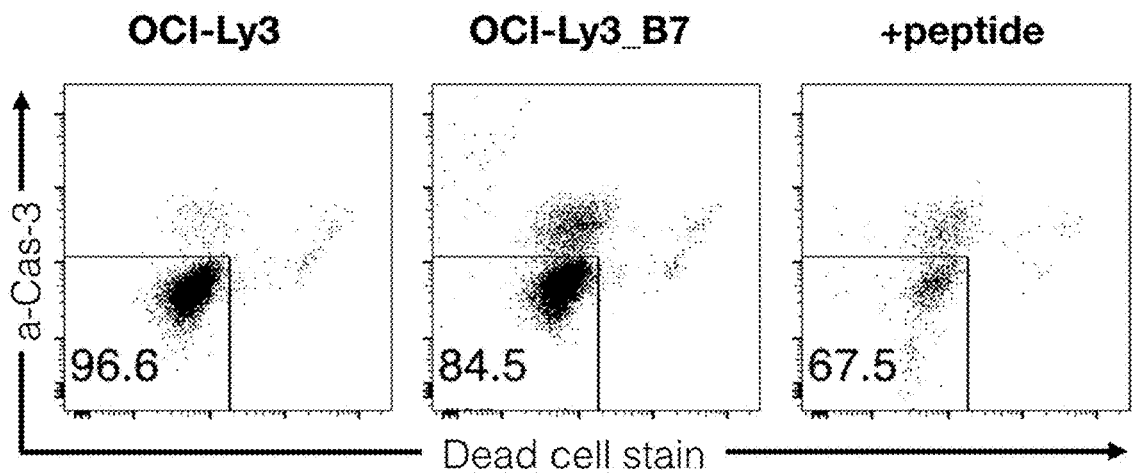
Figure 7:
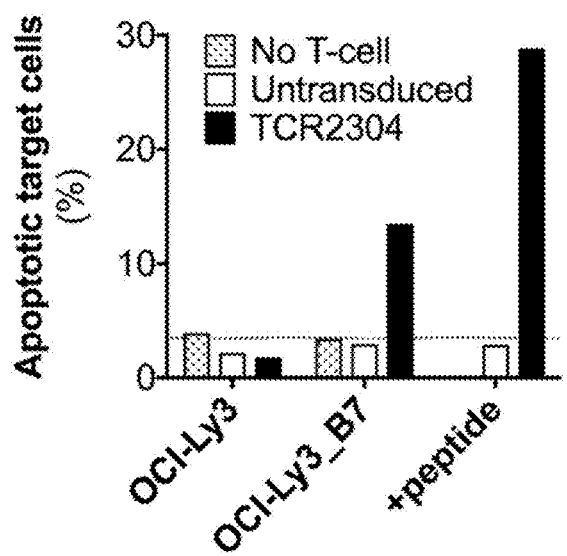
Figure 7:
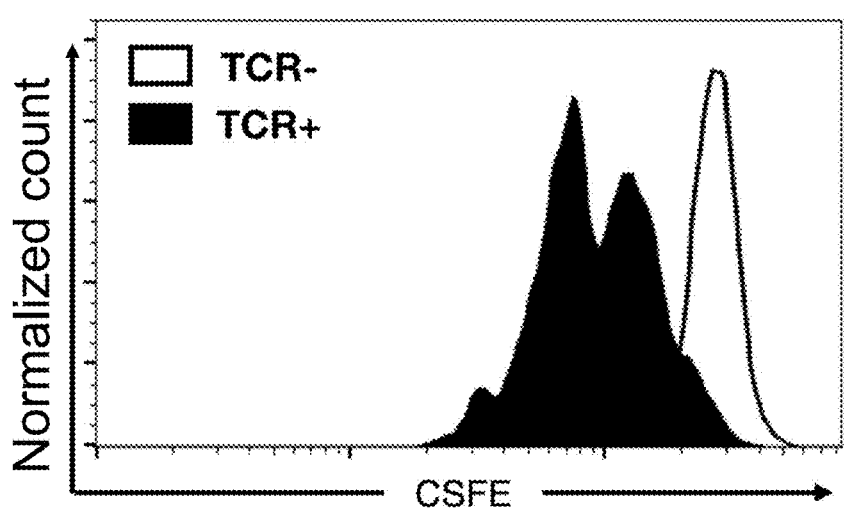
Figure 8:
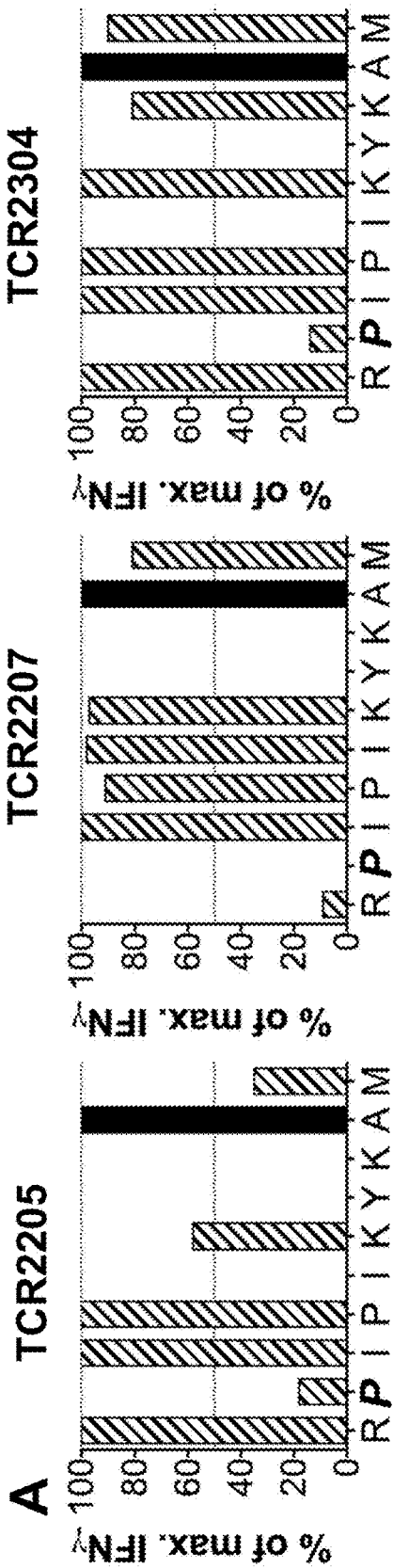
Figure 8:
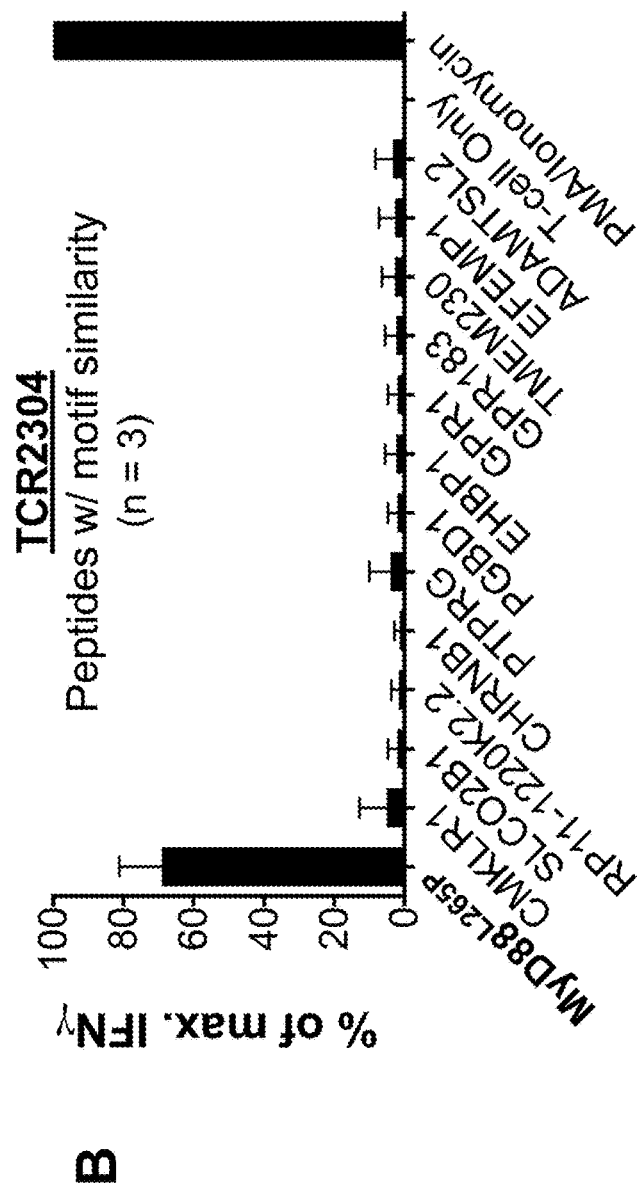
Figure 9:
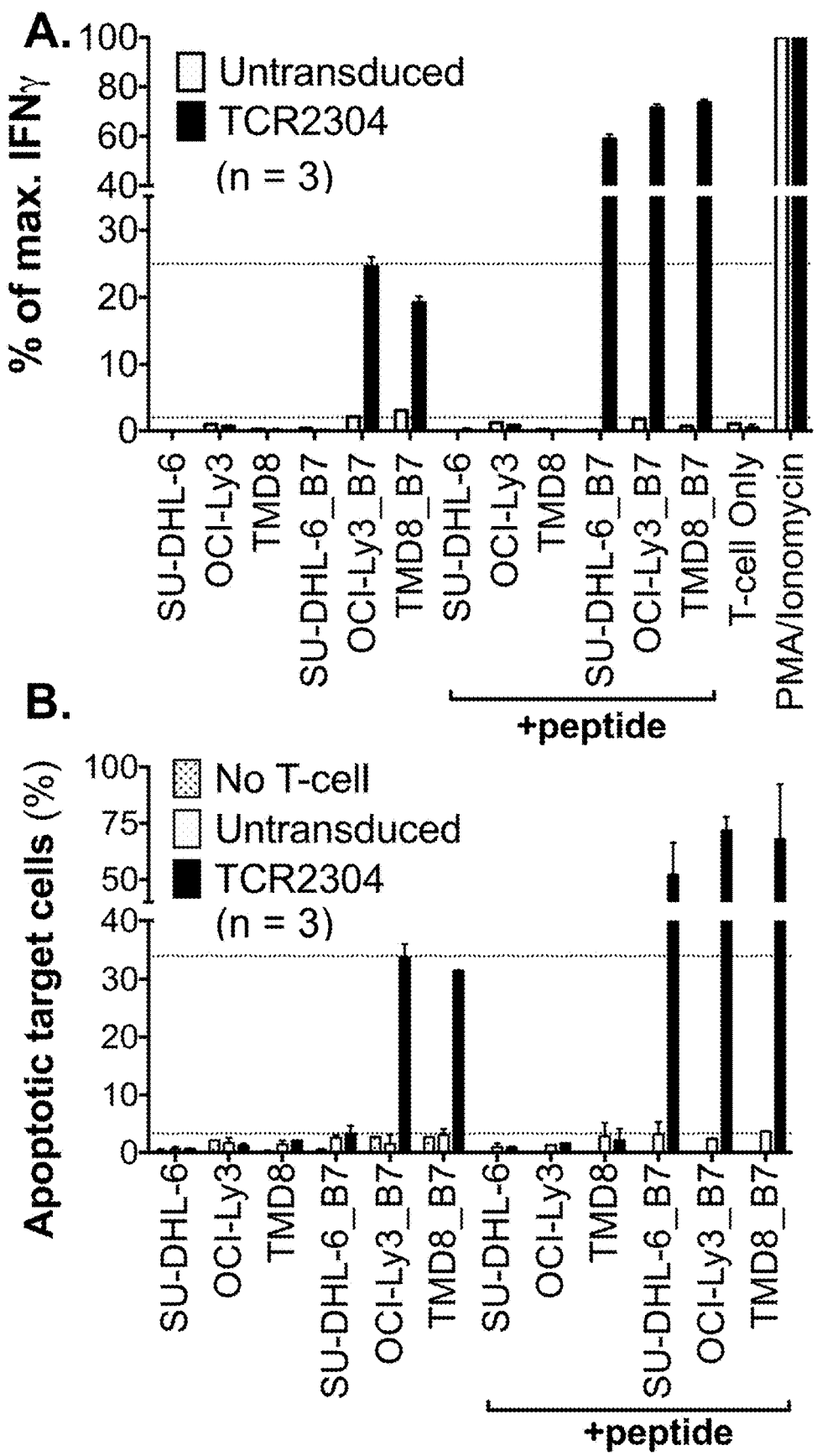
FIG. 9A shows mutation-specific recognition of both OCI-Ly3 and TMD8 cell lines with HLAB7 expression. SU-DHL-6 control cell line with HLA-B7 is only recognized when loaded with mutant peptide before the co-culture.
FIG. 9B shows efficient mutation-specific and HLA-restricted killing of OCI-Ly3 and TMD8 cell lines by TCR-transduced T cells.

```
<160> NUMBER OF SEQ ID NOS: 152

<210> SEQ ID NO 1
<211> LENGTH: 9
<212> TYPE: PRT
<213> ORGANISM: Homo sapiens

<400> SEQUENCE: 1

Arg Pro Ile Pro Ile Lys Tyr Lys Ala
1               5

<210> SEQ ID NO 2
<211> LENGTH: 10
<212> TYPE: PRT
<213> ORGANISM: Homo sapiens

<400> SEQUENCE: 2

Arg Pro Ile Pro Ile Lys Tyr Lys Ala Met
1               5                   10

<210> SEQ ID NO 3
<211> LENGTH: 10
<212> TYPE: PRT
<213> ORGANISM: Homo sapiens

<400> SEQUENCE: 3

Arg Leu Ile Pro Ile Lys Tyr Lys Ala Met
1               5                   10

<210> SEQ ID NO 4

<400> SEQUENCE: 4

000

<210> SEQ ID NO 5
```

```
<211> LENGTH: 136
<212> TYPE: PRT
<213> ORGANISM: Mus musculus

<400> SEQUENCE: 5

Ile Gln Asn Pro Glu Pro Ala Val Tyr Gln Leu Lys Asp Pro Arg Ser
1               5                   10                  15

Gln Asp Ser Thr Leu Cys Leu Phe Thr Asp Phe Asp Ser Gln Ile Asn
            20                  25                  30

Val Pro Lys Thr Met Glu Ser Gly Thr Phe Ile Thr Asp Lys Thr Val
        35                  40                  45

Leu Asp Met Lys Ala Met Asp Ser Lys Ser Asn Gly Ala Ile Ala Trp
    50                  55                  60

Ser Asn Gln Thr Ser Phe Thr Cys Gln Asp Ile Phe Lys Glu Thr Asn
65              70                  75                  80

Ala Thr Tyr Pro Ser Ser Asp Val Pro Cys Asp Ala Thr Leu Thr Glu
            85                  90                  95

Lys Ser Phe Glu Thr Asp Met Asn Leu Asn Phe Gln Asn Leu Ser Val
        100                 105                 110

Met Gly Leu Arg Ile Leu Leu Leu Lys Val Ala Gly Phe Asn Leu Leu
    115                 120                 125

Met Thr Leu Arg Leu Trp Ser Ser
    130                 135

<210> SEQ ID NO 6
<211> LENGTH: 140
<212> TYPE: PRT
<213> ORGANISM: Artificial Sequence
<220> FEATURE:
<223> OTHER INFORMATION: minimally murine constant region - TCR alpha
      chain

<400> SEQUENCE: 6

Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65              70                  75                  80

Ile Pro Glu Asp Thr Phe Phe Pro Ser Ser Asp Val Pro Cys Asp Val
            85                  90                  95

Lys Leu Val Glu Lys Ser Phe Glu Thr Asp Thr Asn Leu Asn Phe Gln
        100                 105                 110

Asn Leu Ser Val Ile Gly Phe Arg Ile Leu Leu Leu Lys Val Ala Gly
    115                 120                 125

Phe Asn Leu Leu Met Thr Leu Arg Leu Trp Ser Ser
    130                 135                 140

<210> SEQ ID NO 7
<211> LENGTH: 140
<212> TYPE: PRT
<213> ORGANISM: Homo sapiens

<400> SEQUENCE: 7
```

```
Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140
```

<210> SEQ ID NO 8
<211> LENGTH: 173
<212> TYPE: PRT
<213> ORGANISM: Mus musculus

<400> SEQUENCE: 8

```
Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr His Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Gly Leu Val Leu Met Ala Met Val Lys Lys Asn Ser
                165                 170
```

<210> SEQ ID NO 9
<211> LENGTH: 179
<212> TYPE: PRT
<213> ORGANISM: Artificial Sequence
<220> FEATURE:
<223> OTHER INFORMATION: minimally murinized contant region - TCR beta chain

<400> SEQUENCE: 9

```
Glu Asp Leu Lys Asn Val Phe Pro Pro Lys Val Ala Val Phe Glu Pro
1               5                   10                  15

Ser Lys Ala Glu Ile Ala His Thr Gln Lys Ala Thr Leu Val Cys Leu
            20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Ile Thr Ser Ala Ser Tyr His Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 10
<211> LENGTH: 179
<212> TYPE: PRT
<213> ORGANISM: Homo sapiens

<400> SEQUENCE: 10

Glu Asp Leu Lys Asn Val Phe Pro Pro Lys Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly
```

<210> SEQ ID NO 11
<211> LENGTH: 6
<212> TYPE: PRT
<213> ORGANISM: Homo sapiens

<400> SEQUENCE: 11

Thr Ser Gly Phe Asn Gly
1               5

<210> SEQ ID NO 12
<211> LENGTH: 6
<212> TYPE: PRT
<213> ORGANISM: Homo sapiens

<400> SEQUENCE: 12

Asn Val Leu Asp Gly Leu
1               5

<210> SEQ ID NO 13
<211> LENGTH: 12
<212> TYPE: PRT
<213> ORGANISM: Homo sapiens

<400> SEQUENCE: 13

Cys Ala Val Asp Val Gly Tyr Ser Thr Leu Thr Phe
1               5                   10

<210> SEQ ID NO 14
<211> LENGTH: 6
<212> TYPE: PRT
<213> ORGANISM: Homo sapiens

<400> SEQUENCE: 14

Asp Phe Gln Ala Thr Thr
1               5

<210> SEQ ID NO 15
<211> LENGTH: 7
<212> TYPE: PRT
<213> ORGANISM: Homo sapiens

<400> SEQUENCE: 15

Ser Asn Glu Gly Ser Lys Ala
1               5

<210> SEQ ID NO 16
<211> LENGTH: 16
<212> TYPE: PRT
<213> ORGANISM: Homo sapiens

<400> SEQUENCE: 16

Cys Ser Ala Arg Asp Arg Ser Gly Thr Leu Gly Gly Glu Leu Phe Phe
1               5                   10                  15

<210> SEQ ID NO 17
<211> LENGTH: 127
<212> TYPE: PRT
<213> ORGANISM: Homo sapiens

<400> SEQUENCE: 17

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
                20                  25                  30

Ala Ile Val Gln Ile Asn Cys Thr Tyr Gln Thr Ser Gly Phe Asn Gly
              35                  40                  45

Leu Phe Trp Tyr Gln Gln His Ala Gly Glu Ala Pro Thr Phe Leu Ser
 50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Val Asp Val Gly Tyr Ser
               100                 105                 110

Thr Leu Thr Phe Gly Lys Gly Thr Met Leu Leu Val Ser Pro Asp
           115                 120                 125

<210> SEQ ID NO 18
<211> LENGTH: 132
<212> TYPE: PRT
<213> ORGANISM: Homo sapiens

<400> SEQUENCE: 18

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
                20                  25                  30

Val Lys Ile Glu Cys Arg Ser Leu Asp Phe Gln Ala Thr Thr Met Phe
              35                  40                  45

Trp Tyr Arg Gln Phe Pro Lys Gln Ser Leu Met Leu Met Ala Thr Ser
 50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Arg Asp
               100                 105                 110

Arg Ser Gly Thr Leu Gly Gly Glu Leu Phe Phe Gly Glu Gly Ser Arg
           115                 120                 125

Leu Thr Val Leu
        130

<210> SEQ ID NO 19
<211> LENGTH: 381
<212> TYPE: DNA
<213> ORGANISM: Artificial Sequence
<220> FEATURE:
<223> OTHER INFORMATION: alpha chain variable region of TCR2207 - codon
      optimized

<400> SEQUENCE: 19
atgtggggcg tgttcctgct gtacgtgtcc atgaagatgg cggcaccac cggccagaac      60 atcgatcagc tacagagat gaccgccacc gagggcgcca tcgtgcagat caattgcacc     120
taccagacca gcggcttcaa cgggctgttt tggtatcagc agcacgccgg cgaggcccct    180
acattcctga gctacaatgt gctggacggc ctcgaggaaa aggcagatt ctccagcttc     240 ctgagcagaa gcaagggcta ctcctacctg ctgctgaaag aactgcagat gaaggacagc    300
gcctcttacc tgtgcgccgt ggatgtgggc tacagcacac tgacatttgg caagggcacc    360
atgctgctcg tgtccccaga c                                             381

<210> SEQ ID NO 20
<211> LENGTH: 396
<212> TYPE: DNA
<213> ORGANISM: Artificial Sequence
<220> FEATURE:
<223> OTHER INFORMATION: beta chain variable region of TCR2207 - codon
      optimized

<400> SEQUENCE: 20

```
atgttgttgt tgctgttgct cctcggacct ggctctggac tgggagctgt ggtttctcag      60
cacccctctt gggtcatctg caagagcggc accagcgtga agatcgagtg cagaagcctg     120
gacttccagg ccaccacaat gttctggtac agacagttcc ccaagcagag cctgatgctg     180
atggccacct ctaacgaggg cagcaaggcc acatatgagc agggcgtcga aggacaag      240 ttcctgatca accacgccag cctgacactg agcaccctga cagtgacaag cgcccatcct     300
gaggacagca gcttctacat ctgcagcgcc agagacagaa gcggcacact tggcggcgag     360 ctgtttttg gcgagggctc tagactgacc gtgctg                               396
```

<210> SEQ ID NO 21
<211> LENGTH: 7
<212> TYPE: PRT
<213> ORGANISM: Homo sapiens

<400> SEQUENCE: 21

Asn Ile Ala Thr Asn Asp Tyr
1               5

<210> SEQ ID NO 22
<211> LENGTH: 5
<212> TYPE: PRT
<213> ORGANISM: Homo sapiens

<400> SEQUENCE: 22

Gly Tyr Lys Thr Lys
1               5

<210> SEQ ID NO 23
<211> LENGTH: 14
<212> TYPE: PRT
<213> ORGANISM: Homo sapiens

<400> SEQUENCE: 23

Cys Leu Val Gly Arg Asp Gly Gly Ser Tyr Ile Pro Thr Phe
1               5                   10

<210> SEQ ID NO 24
<211> LENGTH: 5
<212> TYPE: PRT
<213> ORGANISM: Homo sapiens

<400> SEQUENCE: 24

Ser Gly Asp Leu Ser
1               5

<210> SEQ ID NO 25
<211> LENGTH: 6
<212> TYPE: PRT
<213> ORGANISM: Homo sapiens

<400> SEQUENCE: 25

Tyr Tyr Asn Gly Glu Glu
1               5

<210> SEQ ID NO 26
<211> LENGTH: 14
<212> TYPE: PRT
<213> ORGANISM: Homo sapiens

<400> SEQUENCE: 26

Cys Ala Ser Ser Ala Gly Gln Gly Ala Tyr Glu Gln Tyr Phe
1               5                   10

<210> SEQ ID NO 27
<211> LENGTH: 129
<212> TYPE: PRT
<213> ORGANISM: Homo sapiens

<400> SEQUENCE: 27

Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Gly Arg Asp Gly Gly
            100                 105                 110

Ser Tyr Ile Pro Thr Phe Gly Arg Gly Thr Ser Leu Ile Val His Pro
        115                 120                 125

Tyr

<210> SEQ ID NO 28
<211> LENGTH: 132
<212> TYPE: PRT
<213> ORGANISM: Homo sapiens

<400> SEQUENCE: 28

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile His Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Ala Gly Gln Gly Ala Tyr Glu Gln Tyr Phe Gly Pro Gly Thr Arg
        115                 120                 125

Leu Thr Val Thr
        130

<210> SEQ ID NO 29
<211> LENGTH: 387
<212> TYPE: DNA
<213> ORGANISM: Artificial Sequence
<220> FEATURE:
<223> OTHER INFORMATION: alpha chain variable region of TCR2205 - codon-
      optimized

<400> SEQUENCE: 29
atgagacagg tggccagagt gatcgtgttc ctgacactga gcaccctgag cctggccaag      60
accacacagc ccatcagcat ggacagctac gagggccaag aagtgaacat cacctgtagc     120
cacaacaata tcgccaccaa cgactacatc acgtggtatc aacagttccc cagtcaaggc     180
cctcggttca tcatccaagg ctacaagacc aaagtgacca cgaggtggc ctctctgttc      240 atccccgccg acagaaagag cagcaccctg tctctgccta gagtgtccct gagcgatacc     300
gccgtgtact actgtctcgt gggcagagat ggcggcagct acatccctac atttggcaga     360
ggcacaagcc tgatcgtgca cccctac                                         387

<210> SEQ ID NO 30
<211> LENGTH: 396
<212> TYPE: DNA
<213> ORGANISM: Artificial Sequence
<220> FEATURE:
<223> OTHER INFORMATION: beta chain variable region of TCR2205 - codon-
      optimized

<400> SEQUENCE: 30
atgggtttta gactgctgtg ctgcgtggcc ttctgtctgc ttggagctgg ccctgtggat      60
agcggcgtta cccagacacc taagcacctg atcacagcca caggccagcg cgtgaccctg     120
agatgttctc ctagaagcgg cgacctgagc gtgtactggt atcagcagtc tctggaccag     180
ggcctgcagt tcctgatcca ctactacaac ggcgaggaaa gagccaaggg caacatcctg     240
gaacggttca gcgcccagca gttcccagat ctgcacagcg agctgaacct gagcagcctg     300
gaactgggag atagcgccct gtacttctgt gcctcttctg ctggacaggg cgcctacgag     360
cagtattttg gccctggcac cagactgacc gtgacc                               396

<210> SEQ ID NO 31
<211> LENGTH: 6
<212> TYPE: PRT
<213> ORGANISM: Homo sapiens

<400> SEQUENCE: 31

Asp Ser Ala Ile Tyr Asn
1               5

<210> SEQ ID NO 32
<211> LENGTH: 7
<212> TYPE: PRT
<213> ORGANISM: Homo sapiens

<400> SEQUENCE: 32

Ile Gln Ser Ser Gln Arg Glu
1               5

<210> SEQ ID NO 33
<211> LENGTH: 13
<212> TYPE: PRT
<213> ORGANISM: Homo sapiens

```
<400> SEQUENCE: 33

Cys Ala Pro Leu Gly Gly Gly Tyr Asn Lys Leu Ile Phe
1               5                   10

<210> SEQ ID NO 34
<211> LENGTH: 5
<212> TYPE: PRT
<213> ORGANISM: Homo sapiens

<400> SEQUENCE: 34

Met Asn His Asn Tyr
1               5

<210> SEQ ID NO 35
<211> LENGTH: 6
<212> TYPE: PRT
<213> ORGANISM: Homo sapiens

<400> SEQUENCE: 35

Ser Val Gly Ala Gly Ile
1               5

<210> SEQ ID NO 36
<211> LENGTH: 14
<212> TYPE: PRT
<213> ORGANISM: Homo sapiens

<400> SEQUENCE: 36

Cys Ala Ser Arg Leu Pro Thr Thr Asp Glu Lys Leu Phe Phe
1               5                   10

<210> SEQ ID NO 37
<211> LENGTH: 131
<212> TYPE: PRT
<213> ORGANISM: Homo sapiens

<400> SEQUENCE: 37

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
        50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Pro Leu
            100                 105                 110

Gly Gly Gly Tyr Asn Lys Leu Ile Phe Gly Ala Gly Thr Arg Leu Ala
        115                 120                 125

Val His Pro
        130

<210> SEQ ID NO 38
<211> LENGTH: 132
<212> TYPE: PRT
<213> ORGANISM: Homo sapiens
```

<400> SEQUENCE: 38

Met Ser Ile Ser Leu Leu Cys Cys Ala Ala Phe Pro Leu Leu Trp Ala
1               5                   10                  15

Gly Pro Val Asn Ala Gly Val Thr Gln Thr Pro Lys Phe Arg Ile Leu
            20                  25                  30

Lys Ile Gly Gln Ser Met Thr Leu Gln Cys Ala Gln Asp Met Asn His
        35                  40                  45

Asn Tyr Met Tyr Trp Tyr Arg Gln Asp Pro Gly Met Gly Leu Lys Leu
    50                  55                  60

Ile Tyr Tyr Ser Val Gly Ala Gly Ile Thr Asp Lys Gly Glu Val Pro
65                  70                  75                  80

Asn Gly Tyr Asn Val Ser Arg Ser Thr Thr Glu Asp Phe Pro Leu Arg
                85                  90                  95

Leu Glu Leu Ala Ala Pro Ser Gln Thr Ser Val Tyr Phe Cys Ala Ser
            100                 105                 110

Arg Leu Pro Thr Thr Asp Glu Lys Leu Phe Phe Gly Ser Gly Thr Gln
            115                 120                 125

Leu Ser Val Leu
    130

<210> SEQ ID NO 39
<211> LENGTH: 393
<212> TYPE: DNA
<213> ORGANISM: Artificial Sequence
<220> FEATURE:
<223> OTHER INFORMATION: alpha chain variable region of TCR1610 - codon
      optimized

<400> SEQUENCE: 39
atggaaacac tgctgggcct gctgatcctg tggctgcaac tgcaatgggt gtcctccaag        60
caagaagtga ctcagatccc tgccgctctg tccgtgcctg aaggcgaaaa cctggtcctg       120
aactgcagct tcaccgacag cgccatctac aacctgcagt ggttcaggca ggatccaggc       180
aagggactga cctctctgct gctgattcag agcagccaga gagagcagac ctccggcaga       240
ctgaatgcca gctggataaa gagcagcggc cggtctacac tgtatatcgc cgcttctcag       300
ccaggcgata gcgccacata tctgtgtgct cctctcggcg aggctacaa caagctgatt        360 ttcggcgctg gcaccagact ggccgtgcat cct                                    393

<210> SEQ ID NO 40
<211> LENGTH: 396
<212> TYPE: DNA
<213> ORGANISM: Artificial Sequence
<220> FEATURE:
<223> OTHER INFORMATION: beta chain variable region of TCR1610 - codon
      optimized

<400> SEQUENCE: 40
atgtctatta gcctgctgtg ctgtgccgcc tttcctctgc tttgggccgg acctgttaat        60
gccggcgtga cccagacacc taagttccgg atcctgaaga tcggccagag catgaccctg       120
cagtgcgccc aggacatgaa ccacaactac atgtactggt acagacagga ccccggcatg       180
ggcctgaagc tgatctacta ttctgtcgga gccggcatca ccgacaaggg cgaagtgcct       240
aatggctaca acgtgtccag aagcaccacc gaggacttcc ctctgcgact ggaactggct       300
gccccatctc agaccagcgt gtacttctgt gccagcagac tgcccaccac cgacgagaag       360
ctgttttttg gcagcggcac ccagctgagc gtgctg                                 396

<210> SEQ ID NO 41
<211> LENGTH: 6
<212> TYPE: PRT
<213> ORGANISM: Homo sapiens

<400> SEQUENCE: 41

Asn Ser Ala Ser Asp Tyr
1               5

<210> SEQ ID NO 42
<211> LENGTH: 7
<212> TYPE: PRT
<213> ORGANISM: Homo sapiens

<400> SEQUENCE: 42

Ile Arg Ser Asn Met Asp Lys
1               5

<210> SEQ ID NO 43
<211> LENGTH: 13
<212> TYPE: PRT
<213> ORGANISM: Homo sapiens

<400> SEQUENCE: 43

Cys Ala Glu Gly Thr Gly Ser Ala Arg Gln Leu Thr Phe
1               5                   10

<210> SEQ ID NO 44
<211> LENGTH: 5
<212> TYPE: PRT
<213> ORGANISM: Homo sapiens

<400> SEQUENCE: 44

Met Asp His Glu Asn
1               5

<210> SEQ ID NO 45
<211> LENGTH: 6
<212> TYPE: PRT
<213> ORGANISM: Homo sapiens

<400> SEQUENCE: 45

Ser Tyr Asp Val Lys Met
1               5

<210> SEQ ID NO 46
<211> LENGTH: 20
<212> TYPE: PRT
<213> ORGANISM: Homo sapiens

<400> SEQUENCE: 46

Cys Ala Ser Gly Pro Phe Arg Asp Ser Val Leu Thr Leu Val Ala Asn
1               5                   10                  15

Val Leu Thr Phe
            20

<210> SEQ ID NO 47
<211> LENGTH: 132
<212> TYPE: PRT
<213> ORGANISM: Homo sapiens

<400> SEQUENCE: 47

Met Ala Gly Ile Arg Ala Leu Phe Met Tyr Leu Trp Leu Gln Leu Asp
1               5                   10                  15

Trp Val Ser Arg Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Ser Gly Lys Gly Pro
50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Gly Thr Gly Ser Ala Arg Gln Leu Thr Phe Gly Ser Gly Thr Gln Leu
            115                 120                 125

Thr Val Leu Pro
    130

<210> SEQ ID NO 48
<211> LENGTH: 138
<212> TYPE: PRT
<213> ORGANISM: Homo sapiens

<400> SEQUENCE: 48

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Gly Pro Phe Arg Asp Ser Val Leu Thr Leu Val Ala Asn Val Leu Thr
            115                 120                 125

Phe Gly Ala Gly Ser Arg Leu Thr Val Leu
    130                 135

<210> SEQ ID NO 49
<211> LENGTH: 396
<212> TYPE: DNA
<213> ORGANISM: Artificial Sequence
<220> FEATURE:
<223> OTHER INFORMATION: alpha chain variable region of TCR1605 - codon
      optimized

<400> SEQUENCE: 49
atggccggaa tcagagccct gttcatgtat ctgtggctgc agctggactg ggtgtccagg      60
ggagaatctg tcggactgca tctgcccaca ctgagcgtgc aagagggcga caacagcatc     120
atcaactgcg cctacagcaa cagcgcctcc gactacttca tctggtacaa gcaagagagc     180
ggcaagggcc ctcagttcat catcgacatc cggtccaaca tggacaagcg gcaaggccag     240

```
agagtgaccg tcctgctgaa caagaccgtg aagcacctga gcctgcagat cgccgctaca    300
cagcctggcg atagcgccgt gtacttttgt gctgaaggca ccggaagcgc cagacagctg    360
acatttggca gcggaaccca gctcacagtg ctgccc                              396
```

<210> SEQ ID NO 50
<211> LENGTH: 414
<212> TYPE: DNA
<213> ORGANISM: Artificial Sequence
<220> FEATURE:
<223> OTHER INFORMATION: beta chain variable region of TCR1605 - codon
      optimized

<400> SEQUENCE: 50

```
atgggaatta gactgctgtg cagagtggcc ttctgcttcc tggctgttgg cctggtggac     60
gtgaaagtga cccagagcag cagataccTg gtcaagagaa ccggcgagaa ggtgttcctg    120
gaatgcgtgc aggacatgga ccacgagaat atgttctggt acagacagga ccccggcctg    180
ggcctgagac tgatctactt cagctacgac gtgaagatga ggaaaaaggg cgacatcccc    240
gagggctaca gcgtgtccag agagaagaaa gagcggttca gcctgatcct ggaaagcgcc    300
agcaccaacc agaccagcat gtacctgtgt gccagcggac ccttcagaga cagcgtgctg    360
acactggtgg ccaacgtgct gacttttggc gccggaagca gactgaccgt gctg          414
```

<210> SEQ ID NO 51
<211> LENGTH: 7
<212> TYPE: PRT
<213> ORGANISM: Homo sapiens

<400> SEQUENCE: 51

Asn Ile Ala Thr Asn Asp Tyr
1               5

<210> SEQ ID NO 52
<211> LENGTH: 5
<212> TYPE: PRT
<213> ORGANISM: Homo sapiens

<400> SEQUENCE: 52

Gly Tyr Glu Thr Lys
1               5

<210> SEQ ID NO 53
<211> LENGTH: 13
<212> TYPE: PRT
<213> ORGANISM: Homo sapiens

<400> SEQUENCE: 53

Cys Leu Ser Leu Ser Asp Ser Asn Tyr Gln Leu Ile Trp
1               5                   10

<210> SEQ ID NO 54
<211> LENGTH: 5
<212> TYPE: PRT
<213> ORGANISM: Homo sapiens

<400> SEQUENCE: 54

Ser Gly Asp Leu Ser
1               5

<210> SEQ ID NO 55
<211> LENGTH: 6
<212> TYPE: PRT

```
<213> ORGANISM: Homo sapiens

<400> SEQUENCE: 55

Tyr Tyr Asn Gly Glu Glu
1               5

<210> SEQ ID NO 56
<211> LENGTH: 14
<212> TYPE: PRT
<213> ORGANISM: Homo sapiens

<400> SEQUENCE: 56

Cys Ala Ser Ser Val Gly Gln Gly Ser Tyr Glu Gln Tyr Phe
1               5                   10

<210> SEQ ID NO 57
<211> LENGTH: 128
<212> TYPE: PRT
<213> ORGANISM: Homo sapiens

<400> SEQUENCE: 57

Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Ser Leu Ser Asp Ser Asn
            100                 105                 110

Tyr Gln Leu Ile Trp Gly Ala Gly Thr Lys Leu Ile Ile Lys Pro Asp
        115                 120                 125

<210> SEQ ID NO 58
<211> LENGTH: 132
<212> TYPE: PRT
<213> ORGANISM: Homo sapiens

<400> SEQUENCE: 58

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110
```

-continued

```
Ser Val Gly Gln Gly Ser Tyr Glu Gln Tyr Phe Gly Pro Gly Thr Arg
        115                 120                 125

Leu Thr Val Thr
    130

<210> SEQ ID NO 59
<211> LENGTH: 384
<212> TYPE: DNA
<213> ORGANISM: Artificial Sequence
<220> FEATURE:
<223> OTHER INFORMATION: alpha chain variable region of TCR2202 - codon
      optimized

<400> SEQUENCE: 59
atgagacagg tggccagagt gatcgtgttc ctgacactga gcaccctgag cctggccaag     60
accacacagc ccatcagcat ggactcctac gagggccaag aagtgaacat cacctgtagc    120
cacaacaata tcgccaccaa cgactacatc acgtggtatc aacagttccc cagtcaaggc    180
cctcggttca tcatccaagg ctacaagacc aaagtgacca acgaggtggc ctctctgttc    240
atccccgccg atagaaagag cagcaccctg tctctgccca gagtgtccct gagcgatacc    300
gccgtgtact actgtctgag cctgtccgac tccaactacc agctgatttg gggagccggc    360
accaagctga tcatcaagcc cgac                                           384

<210> SEQ ID NO 60
<211> LENGTH: 396
<212> TYPE: PRT
<213> ORGANISM: Artificial Sequence
<220> FEATURE:
<223> OTHER INFORMATION: beta chain variable region of TCR2202 - codon
      optimized

<400> SEQUENCE: 60

Ala Thr Gly Gly Gly Thr Thr Thr Thr Ala Gly Ala Cys Thr Gly Cys
1               5                   10                  15

Thr Gly Thr Gly Cys Thr Gly Cys Gly Thr Gly Gly Cys Cys Thr Thr
            20                  25                  30

Cys Thr Gly Thr Cys Thr Gly Cys Thr Thr Gly Gly Ala Gly Cys Thr
        35                  40                  45

Gly Gly Cys Cys Cys Thr Gly Thr Gly Gly Ala Thr Ala Gly Cys Gly
    50                  55                  60

Gly Cys Gly Thr Thr Ala Cys Cys Cys Ala Gly Ala Cys Ala Cys Cys
65                  70                  75                  80

Thr Ala Ala Gly Cys Ala Cys Cys Thr Gly Ala Thr Cys Ala Cys Ala
                85                  90                  95

Gly Cys Cys Ala Cys Ala Gly Gly Cys Cys Ala Gly Cys Gly Cys Gly
            100                 105                 110

Thr Gly Ala Cys Cys Cys Thr Gly Ala Gly Ala Thr Gly Thr Thr Cys
        115                 120                 125

Thr Cys Cys Thr Ala Gly Ala Ala Gly Cys Gly Gly Cys Gly Ala Cys
    130                 135                 140

Cys Thr Gly Ala Gly Cys Gly Thr Gly Thr Ala Cys Thr Gly Gly Thr
145                 150                 155                 160

Ala Thr Cys Ala Gly Cys Ala Gly Thr Cys Thr Cys Thr Gly Gly Ala
                165                 170                 175

Cys Cys Ala Gly Gly Gly Cys Cys Thr Gly Cys Ala Gly Thr Thr Cys
            180                 185                 190

Cys Thr Gly Ala Thr Cys Cys Ala Gly Thr Ala Cys Thr Ala Cys Ala
```

```
            195                 200                 205
Ala Cys Gly Gly Cys Gly Ala Gly Ala Ala Gly Ala Gly Cys
        210                 215                 220
Cys Ala Ala Gly Gly Cys Ala Ala Cys Ala Thr Cys Cys Thr Gly
225                 230                 235                 240
Gly Ala Ala Cys Gly Gly Thr Thr Cys Ala Gly Cys Gly Cys Cys
                245                 250                 255
Ala Gly Cys Ala Gly Thr Thr Cys Cys Ala Gly Ala Thr Cys Thr
            260                 265                 270
Gly Cys Ala Cys Ala Gly Cys Gly Ala Gly Cys Thr Gly Ala Ala Cys
        275                 280                 285
Cys Thr Gly Ala Gly Cys Ala Gly Cys Cys Thr Gly Gly Ala Ala Cys
        290                 295                 300
Thr Gly Gly Gly Ala Gly Ala Thr Ala Gly Cys Gly Cys Cys Cys Thr
305                 310                 315                 320
Gly Thr Ala Cys Thr Thr Cys Thr Gly Thr Gly Cys Thr Cys Thr
                325                 330                 335
Thr Cys Thr Gly Thr Cys Gly Gly Cys Cys Ala Gly Gly Cys Ala
                340                 345                 350
Gly Cys Thr Ala Cys Gly Ala Gly Cys Ala Gly Thr Ala Thr Thr
            355                 360                 365
Thr Gly Gly Cys Cys Thr Gly Gly Cys Ala Cys Ala Gly Ala
        370                 375                 380
Cys Thr Gly Ala Cys Cys Gly Thr Gly Ala Cys Cys
385                 390                 395

<210> SEQ ID NO 61
<211> LENGTH: 5
<212> TYPE: PRT
<213> ORGANISM: Homo sapiens

<400> SEQUENCE: 61

Lys Ala Leu Tyr Ser
1               5

<210> SEQ ID NO 62
<211> LENGTH: 7
<212> TYPE: PRT
<213> ORGANISM: Homo sapiens

<400> SEQUENCE: 62

Leu Leu Lys Gly Gly Glu Gln
1               5

<210> SEQ ID NO 63
<211> LENGTH: 15
<212> TYPE: PRT
<213> ORGANISM: Homo sapiens

<400> SEQUENCE: 63

Cys Gly Thr Ala His Leu Arg Ala Gly Ser Tyr Gln Leu Thr Phe
1               5                   10                  15

<210> SEQ ID NO 64
<211> LENGTH: 5
<212> TYPE: PRT
<213> ORGANISM: Homo sapiens

<400> SEQUENCE: 64
```

```
Met Asn His Glu Tyr
1               5
```

\<210\> SEQ ID NO 65
\<211\> LENGTH: 6
\<212\> TYPE: PRT
\<213\> ORGANISM: Homo sapiens

\<400\> SEQUENCE: 65

```
Ser Met Asn Val Glu Val
1               5
```

\<210\> SEQ ID NO 66
\<211\> LENGTH: 16
\<212\> TYPE: PRT
\<213\> ORGANISM: Homo sapiens

\<400\> SEQUENCE: 66

```
Cys Ala Ser Ser Ser Ser Gly Gly Ala Phe Asn Glu Gln Phe Phe
1               5                   10                  15
```

\<210\> SEQ ID NO 67
\<211\> LENGTH: 134
\<212\> TYPE: PRT
\<213\> ORGANISM: Homo sapiens

\<400\> SEQUENCE: 67

```
Met Glu Thr Leu Leu Lys Val Leu Ser Gly Thr Leu Leu Trp Gln Leu
1               5                   10                  15

Thr Trp Val Arg Ser Gln Gln Pro Val Gln Ser Pro Gln Ala Val Ile
            20                  25                  30

Leu Arg Glu Gly Glu Asp Ala Val Ile Asn Cys Ser Ser Ser Lys Ala
        35                  40                  45

Leu Tyr Ser Val His Trp Tyr Arg Gln Lys His Gly Glu Ala Pro Val
    50                  55                  60

Phe Leu Met Ile Leu Leu Lys Gly Gly Glu Gln Met Arg His Glu Lys
65                  70                  75                  80

Ile Phe Ala Ser Phe Asn Glu Lys Lys Gln Gln Ser Ser Leu Tyr Leu
                85                  90                  95

Thr Ala Ser Gln Leu Ser Tyr Ser Gly Thr Tyr Phe Cys Gly Thr Ala
            100                 105                 110

His Leu Arg Ala Gly Ser Tyr Gln Leu Thr Phe Gly Lys Gly Thr Lys
        115                 120                 125

Leu Ser Val Ile Pro Asn
    130
```

\<210\> SEQ ID NO 68
\<211\> LENGTH: 134
\<212\> TYPE: PRT
\<213\> ORGANISM: Homo sapiens

\<400\> SEQUENCE: 68

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60
```

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
            85                  90                  95

Leu Glu Ser Pro Ser Pro Asn Gln Thr Ser Leu Tyr Phe Cys Ala Ser
                100                 105                 110

Ser Ser Ser Ser Gly Gly Ala Phe Asn Glu Gln Phe Phe Gly Pro Gly
            115                 120                 125

Thr Arg Leu Thr Val Leu
            130

```
<210> SEQ ID NO 69
<211> LENGTH: 402
<212> TYPE: DNA
<213> ORGANISM: Artificial Sequence
<220> FEATURE:
<223> OTHER INFORMATION: alpha chain variable region of TCR2219 - codon
      optimized

<400> SEQUENCE: 69
atggaaaccc tgctgaaggt gctgagcggc acactgctgt ggcagctgac atgggtccga      60
tctcagcagc ctgtgcagtc tcctcaggct gtgatcctga gagaaggcga ggacgccgtg     120
atcaactgca gcagctctaa ggccctgtac agcgtgcact ggtacaggca gaaacacggc     180
gaggcccctg tgttcctgat gattctgctg aaaggcggcg agcagatgcg gcacgagaag     240
atctttgcca gcttcaatga gaagaagcag cagagcagtc tgtacctgac cgccagccag     300
ctgagctaca gcggcacata cttttgcggc acagcccacc tgagagccgg cagctatcag     360
ctgacctttg gcaagggcac aaagctgagc gtgatcccca ac                        402

<210> SEQ ID NO 70
<211> LENGTH: 402
<212> TYPE: DNA
<213> ORGANISM: Artificial Sequence
<220> FEATURE:
<223> OTHER INFORMATION: beta chain variable region of TCR2219 - codon
      optimized

<400> SEQUENCE: 70
atgggacctc aactgctggg atatgtggtg ctgtgtctgc tcggagccgg acctctggaa      60
gctcaagtga cacagaaccc cagatacctg atcaccgtga ccggcaagaa actgaccgtg     120
acctgcagcc agaacatgaa ccacgagtac atgagctggt acagacagga ccctggcctg     180
ggcctgagac agatctacta cagcatgaac gtggaagtga ccgacaaggg cgacgtgccc     240
gagggctaca aggtgtccag aaaagagaag cggaacttcc cactgatcct ggaaagccca     300
tctcctaacc agaccagcct gtacttctgc gccagcagca gttctagcgg cggagccttc     360
aacgagcagt tctttggccc tggcaccagg ctgaccgtgc tg                        402

<210> SEQ ID NO 71
<211> LENGTH: 6
<212> TYPE: PRT
<213> ORGANISM: Homo sapiens

<400> SEQUENCE: 71

Asp Ser Ala Ser Asn Tyr
1               5

<210> SEQ ID NO 72
```

```
<211> LENGTH: 7
<212> TYPE: PRT
<213> ORGANISM: Homo sapiens

<400> SEQUENCE: 72

Ile Arg Ser Asn Val Gly Glu
1               5

<210> SEQ ID NO 73
<211> LENGTH: 13
<212> TYPE: PRT
<213> ORGANISM: Homo sapiens

<400> SEQUENCE: 73

Cys Ala Ala Ser Gly Arg Tyr Asp Tyr Lys Leu Ser Phe
1               5                   10

<210> SEQ ID NO 74
<211> LENGTH: 5
<212> TYPE: PRT
<213> ORGANISM: Homo sapiens

<400> SEQUENCE: 74

Leu Asn His Asn Val
1               5

<210> SEQ ID NO 75
<211> LENGTH: 6
<212> TYPE: PRT
<213> ORGANISM: Homo sapiens

<400> SEQUENCE: 75

Tyr Tyr Asp Lys Asp Phe
1               5

<210> SEQ ID NO 76
<211> LENGTH: 17
<212> TYPE: PRT
<213> ORGANISM: Homo sapiens

<400> SEQUENCE: 76

Cys Ala Thr Ala Ser Asp Leu Gln Gly Asp Arg Ser Thr Glu Ala Phe
1               5                   10                  15

Phe

<210> SEQ ID NO 77
<211> LENGTH: 131
<212> TYPE: PRT
<213> ORGANISM: Homo sapiens

<400> SEQUENCE: 77

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
```

```
                    85                  90                  95
Thr Glu Thr Gln Pro Glu Asp Ser Ala Val Tyr Phe Cys Ala Ala Ser
                100                 105                 110

Gly Arg Tyr Asp Tyr Lys Leu Ser Phe Gly Ala Gly Thr Thr Val Thr
            115                 120                 125

Val Arg Ala
    130

<210> SEQ ID NO 78
<211> LENGTH: 135
<212> TYPE: PRT
<213> ORGANISM: Homo sapiens

<400> SEQUENCE: 78

Met Gly Pro Gly Leu Leu His Trp Met Ala Leu Cys Leu Leu Gly Thr
1               5                   10                  15

Gly His Gly Asp Ala Met Val Ile Gln Asn Pro Arg Tyr Gln Val Thr
            20                  25                  30

Gln Phe Gly Lys Pro Val Thr Leu Ser Cys Ser Gln Thr Leu Asn His
        35                  40                  45

Asn Val Met Tyr Trp Tyr Gln Gln Lys Ser Ser Gln Ala Pro Lys Leu
    50                  55                  60

Leu Phe His Tyr Tyr Asp Lys Asp Phe Asn Asn Glu Ala Asp Thr Pro
65                  70                  75                  80

Asp Asn Phe Gln Ser Arg Arg Pro Asn Thr Ser Phe Cys Phe Leu Asp
                85                  90                  95

Ile Arg Ser Pro Gly Leu Gly Asp Ala Ala Met Tyr Leu Cys Ala Thr
                100                 105                 110

Ala Ser Asp Leu Gln Gly Asp Arg Ser Thr Glu Ala Phe Phe Gly Gln
            115                 120                 125

Gly Thr Arg Leu Thr Val Val
        130                 135

<210> SEQ ID NO 79
<211> LENGTH: 393
<212> TYPE: DNA
<213> ORGANISM: Artificial Sequence
<220> FEATURE:
<223> OTHER INFORMATION: alpha chain variable region of TCR1336 - codon
      optimized

<400> SEQUENCE: 79
atgaccagca tccgggccgt gttcatcttc ctgtggctgc agctggacct cgtgaacggc      60
gagaatgttg agcagcaccc cagcacactg agcgtgcaag agggcgattc tgccgtgatc    120
aagtgcaccc tacagcgaca gcgcctccaa ctacttcccc tggtacaagc agagctggga    180
aaaagacccc agctgatcat cgacatccgg tccaacgtgg gcgagaagaa ggaccagaga    240
atcgccgtga ctctgaacaa gaccgccaag cacttctccc tgcacatcac cgagacacag    300
cctgaggata gcgccgtgta cttttgtgcc gccagcggca gatacgacta caagctgtct    360
tttggcgccg gaaccaccgt gacagtgcgg gcc                                 393

<210> SEQ ID NO 80
<211> LENGTH: 405
<212> TYPE: DNA
<213> ORGANISM: Artificial Sequence
<220> FEATURE:
<223> OTHER INFORMATION: beta chain variable region of TCR1336 - codon
      optimized
```

<400> SEQUENCE: 80

| | | | | | | |
|---|---|---|---|---|---|---|
| atgggacctg | gattgcttca | ttggatggcc | ctgtgtctgc | tcggcacagg | acatggcgac | 60 |
| gctatggtca | ttcagaaccc | cagataccaa | gtgacccagt | tcggcaagcc | cgtgacactg | 120 |
| agctgtagcc | agacactgaa | ccacaacgtg | atgtactggt | atcagcagaa | gtcctctcag | 180 |
| gcccctaagc | tgctgttcca | ctactacgac | aaggacttca | caacgaggc | cgacacaccc | 240 |
| gacaacttcc | agagcagaag | gcccaatacc | agcttctgct | tcctggacat | cagaagccct | 300 |
| ggcctgggag | atgccgccat | gtatctgtgt | gccacagcca | gcgatctgca | gggcgataga | 360 |
| agcaccgagg | ccttttttgg | ccaaggcacc | agactgaccg | tggtg | | 405 |

<210> SEQ ID NO 81
<211> LENGTH: 7
<212> TYPE: PRT
<213> ORGANISM: Homo sapiens

<400> SEQUENCE: 81

Thr Ile Ser Gly Asn Glu Tyr
1               5

<210> SEQ ID NO 82
<211> LENGTH: 5
<212> TYPE: PRT
<213> ORGANISM: Homo sapiens

<400> SEQUENCE: 82

Gly Leu Lys Asn Asn
1               5

<210> SEQ ID NO 83
<211> LENGTH: 15
<212> TYPE: PRT
<213> ORGANISM: Homo sapiens

<400> SEQUENCE: 83

Cys Ile Val Arg Val Met Lys Thr Ser Tyr Asp Lys Val Ile Phe
1               5                   10                  15

<210> SEQ ID NO 84
<211> LENGTH: 5
<212> TYPE: PRT
<213> ORGANISM: Homo sapiens

<400> SEQUENCE: 84

Trp Asn His Asn Asn
1               5

<210> SEQ ID NO 85
<211> LENGTH: 6
<212> TYPE: PRT
<213> ORGANISM: Homo sapiens

<400> SEQUENCE: 85

Ser Tyr Gly Val His Asp
1               5

<210> SEQ ID NO 86
<211> LENGTH: 18
<212> TYPE: PRT
<213> ORGANISM: Homo sapiens

<400> SEQUENCE: 86

Cys Ala Ser Ser Glu Pro Arg Thr Ser Gly Ile Ser Tyr Asn Glu Gln
1               5                   10                  15

Phe Phe

<210> SEQ ID NO 87
<211> LENGTH: 130
<212> TYPE: PRT
<213> ORGANISM: Homo sapiens

<400> SEQUENCE: 87

Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
                20                  25                  30

Arg Ala Ala Asn Leu Pro Cys Asn His Ser Thr Ile Ser Gly Asn Glu
            35                  40                  45

Tyr Val Tyr Trp Tyr Arg Gln Ile His Ser Gln Gly Pro Gln Tyr Ile
        50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Val Met Lys Thr
            100                 105                 110

Ser Tyr Asp Lys Val Ile Phe Gly Pro Gly Thr Ser Leu Ser Val Ile
        115                 120                 125

Pro Asn
    130

<210> SEQ ID NO 88
<211> LENGTH: 136
<212> TYPE: PRT
<213> ORGANISM: Homo sapiens

<400> SEQUENCE: 88

Met Gly Thr Arg Leu Phe Phe Tyr Val Ala Leu Cys Leu Leu Trp Ala
1               5                   10                  15

Gly His Arg Asp Ala Glu Ile Thr Gln Ser Pro Arg His Lys Ile Thr
                20                  25                  30

Glu Thr Gly Arg Gln Val Thr Leu Ala Cys His Gln Thr Trp Asn His
            35                  40                  45

Asn Asn Met Phe Trp Tyr Arg Gln Asp Leu Gly His Gly Leu Arg Leu
        50                  55                  60

Ile His Tyr Ser Tyr Gly Val His Asp Thr Asn Lys Gly Glu Val Ser
65                  70                  75                  80

Asp Gly Tyr Ser Val Ser Arg Ser Asn Thr Glu Asp Leu Pro Leu Thr
                85                  90                  95

Leu Glu Ser Ala Ala Ser Ser Gln Thr Ser Val Tyr Phe Cys Ala Ser
            100                 105                 110

Ser Glu Pro Arg Thr Ser Gly Ile Ser Tyr Asn Glu Gln Phe Phe Gly
        115                 120                 125

Pro Gly Thr Arg Leu Thr Val Leu
    130                 135

<210> SEQ ID NO 89
<211> LENGTH: 390

```
<212> TYPE: DNA
<213> ORGANISM: Artificial Sequence
<220> FEATURE:
<223> OTHER INFORMATION: alpha chain variable region of TCR2211 - codon
      optimized

<400> SEQUENCE: 89
atgagactgg tggccagagt gacagtgttc ctgaccttcg gcaccatcat cgacgccaag        60
acaacccagc tcctagcat ggattgtgcc gagggcagag ctgccaacct gccttgtaat       120
cacagcacca tcagcggcaa cgagtacgtg tactggtaca ggcagatcca ctctcagggc      180
cctcagtaca tcatccacgg actgaagaac aacgagacaa cgagatggc cagcctgatc       240 atcaccgagg atagaaagag cagcaccctg atcctgcctc acgccacact gagagatacc      300
gccgtgtact actgcatcgt gcgcgtgatg aagaccagct acgacaaagt gatctttggc      360
cccggaacca gcctgagcgt gatccccaat                                       390

<210> SEQ ID NO 90
<211> LENGTH: 408
<212> TYPE: DNA
<213> ORGANISM: Artificial Sequence
<220> FEATURE:
<223> OTHER INFORMATION: beta chain variable region of TCR2211 - codon
      optimized

<400> SEQUENCE: 90
atgggaacca gactgttttt ttacgtggcc ctgtgcctgc tgtgggccgg acatagagat        60
gccgagatca cacagagccc agacacaag atcaccgaga caggcagaca agtgaccctg       120
gcctgtcacc agacctggaa ccacaacaac atgttctggt acagacagga cctcggccac      180
ggcctgagac tgatccacta ctcttacggc gtgcacgaca ccaacaaggg cgaagtgtct      240
gacggctaca gcgtgtccag aagcaacacc gaggacctgc ctctgacact ggaatctgcc     300
gccagctctc agaccagcgt gtactttgt gccagcagcg agcctagaac cagcggcatc       360
agctacaacg agcagttctt cggccctggc accagactga ccgtgctg                  408

<210> SEQ ID NO 91
<211> LENGTH: 6
<212> TYPE: PRT
<213> ORGANISM: Homo sapiens

<400> SEQUENCE: 91

Thr Ser Gly Phe Asn Gly
1               5

<210> SEQ ID NO 92
<211> LENGTH: 6
<212> TYPE: PRT
<213> ORGANISM: Homo sapiens

<400> SEQUENCE: 92

Asn Val Leu Asp Gly Leu
1               5

<210> SEQ ID NO 93
<211> LENGTH: 13
<212> TYPE: PRT
<213> ORGANISM: Homo sapiens

<400> SEQUENCE: 93

Cys Ala Val Arg Ala Ser Gly Thr Tyr Lys Tyr Ile Phe
1               5                   10
```

<210> SEQ ID NO 94
<211> LENGTH: 5
<212> TYPE: PRT
<213> ORGANISM: Homo sapiens

<400> SEQUENCE: 94

Ser Gly His Asn Ser
1               5

<210> SEQ ID NO 95
<211> LENGTH: 6
<212> TYPE: PRT
<213> ORGANISM: Homo sapiens

<400> SEQUENCE: 95

Phe Asn Asn Asn Val Pro
1               5

<210> SEQ ID NO 96
<211> LENGTH: 11
<212> TYPE: PRT
<213> ORGANISM: Homo sapiens

<400> SEQUENCE: 96

Cys Ala Ser Gln Asp Ser Tyr Glu Gln Tyr Phe
1               5                   10

<210> SEQ ID NO 97
<211> LENGTH: 128
<212> TYPE: PRT
<213> ORGANISM: Homo sapiens

<400> SEQUENCE: 97

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Val Arg Ala Ser Gly Thr
            100                 105                 110

Tyr Lys Tyr Ile Phe Gly Thr Gly Thr Arg Leu Lys Val Leu Ala Asn
        115                 120                 125

<210> SEQ ID NO 98
<211> LENGTH: 130
<212> TYPE: PRT
<213> ORGANISM: Homo sapiens

<400> SEQUENCE: 98

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
50              55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Gln Asp Ser Tyr Glu Gln Tyr Phe Gly Pro Gly Thr Arg Leu Thr
            115                 120                 125

Val Thr
   130

<210> SEQ ID NO 99
<211> LENGTH: 384
<212> TYPE: DNA
<213> ORGANISM: Artificial Sequence
<220> FEATURE:
<223> OTHER INFORMATION: alpha chain variable region of TCR2304 - codon
      optimized

<400> SEQUENCE: 99
atgtggggcg tgttcctgct gtacgtgtcc atgaagatgg gcggcaccac cggccagaac    60
atcgatcagc ctacagagat gaccgccacc gagggcgcca tcgtgcagat caattgcacc   120
taccagacca gcggcttcaa cgggctgttt tggtatcagc agcacgccgg cgaggcccct   180
acattcctga gctacaatgt gctggacggc tggaagaaa agggcagatt cagcagcttc   240
ctgagcagaa gcaagggcta ctcctacctg ctgctgaaag aactgcagat gaaggacagc   300
gcctcttacc tgtgtgccgt tagagccagc ggcacctaca gtacatcttc ggcaccggc   360 accaggctga aggtgctggc caat                                          384

<210> SEQ ID NO 100
<211> LENGTH: 390
<212> TYPE: DNA
<213> ORGANISM: Artificial Sequence
<220> FEATURE:
<223> OTHER INFORMATION: beta chain variable region of TCR2304 - codon
      optimized

<400> SEQUENCE: 100 atgatagct ggacctttg ttgcgtgtcc ctgtgcatcc tggtggccaa gcacacagat     60
gccggcgtga tccagtctcc tagacacgaa gtgaccgaga tgggccaaga agtgaccctg   120
cgctgcaagc ctatcagcgg ccacaatagc ctgttctggt acagacagac catgatgaga   180
ggcctggaac tgctgatcta cttcaacaac aacgtgccca tcgacgacag cggcatgccc   240
gaggatagat tcagcgccaa gatgcccaac gccagcttca gcaccctgaa gatccagcct   300
agcgagccca gagatagcgc cgtgtacttt tgcgccagcc aggacagcta cgagcagtac   360
tttggccctg gcaccagact gaccgtgacc                                    390

<210> SEQ ID NO 101
<211> LENGTH: 6
<212> TYPE: PRT
<213> ORGANISM: Homo sapiens

<400> SEQUENCE: 101

Asn Ser Ala Phe Gln Tyr
1               5

<210> SEQ ID NO 102
<211> LENGTH: 6
<212> TYPE: PRT
<213> ORGANISM: Homo sapiens

<400> SEQUENCE: 102

Thr Tyr Ser Ser Gly Asn
1               5

<210> SEQ ID NO 103
<211> LENGTH: 13
<212> TYPE: PRT
<213> ORGANISM: Homo sapiens

<400> SEQUENCE: 103

Cys Ala Met Ser Gly Thr Gly Gly Phe Lys Thr Ile Phe
1               5                   10

<210> SEQ ID NO 104
<211> LENGTH: 5
<212> TYPE: PRT
<213> ORGANISM: Homo sapiens

<400> SEQUENCE: 104

Leu Gly His Asn Ala
1               5

<210> SEQ ID NO 105
<211> LENGTH: 6
<212> TYPE: PRT
<213> ORGANISM: Homo sapiens

<400> SEQUENCE: 105

Tyr Ser Leu Glu Glu Arg
1               5

<210> SEQ ID NO 106
<211> LENGTH: 15
<212> TYPE: PRT
<213> ORGANISM: Homo sapiens

<400> SEQUENCE: 106

Cys Ala Ser Ser Gln Asp Arg Pro Asn Tyr Tyr Gly Tyr Thr Phe
1               5                   10                  15

<210> SEQ ID NO 107
<211> LENGTH: 134
<212> TYPE: PRT
<213> ORGANISM: Homo sapiens

<400> SEQUENCE: 107

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Gly Thr Gly Gly Phe Lys Thr Ile Phe Gly Ala Gly Thr Arg
        115                 120                 125

Leu Phe Val Lys Ala Asn
    130

<210> SEQ ID NO 108
<211> LENGTH: 136
<212> TYPE: PRT
<213> ORGANISM: Homo sapiens

<400> SEQUENCE: 108

Met Gly Cys Arg Leu Leu Cys Cys Ala Val Leu Cys Leu Leu Gly Ala
1               5                   10                  15

Gly Glu Leu Val Pro Met Glu Thr Gly Val Thr Gln Thr Pro Arg His
            20                  25                  30

Leu Val Met Gly Met Thr Asn Lys Lys Ser Leu Lys Cys Glu Gln His
        35                  40                  45

Leu Gly His Asn Ala Met Tyr Trp Tyr Lys Gln Ser Ala Lys Lys Pro
    50                  55                  60

Leu Glu Leu Met Phe Val Tyr Ser Leu Glu Glu Arg Val Glu Asn Asn
65                  70                  75                  80

Ser Val Pro Ser Arg Phe Ser Pro Glu Cys Pro Asn Ser Ser His Leu
                85                  90                  95

Phe Leu His Leu His Thr Leu Gln Pro Glu Asp Ser Ala Leu Tyr Leu
            100                 105                 110

Cys Ala Ser Ser Gln Asp Arg Pro Asn Tyr Tyr Gly Tyr Thr Phe Gly
        115                 120                 125

Ser Gly Thr Arg Leu Thr Val Val
    130                 135

<210> SEQ ID NO 109
<211> LENGTH: 402
<212> TYPE: DNA
<213> ORGANISM: Artificial Sequence
<220> FEATURE:
<223> OTHER INFORMATION: alpha chain variable region of TCR2705 - codon
      optimized

<400> SEQUENCE: 109
atgatgaagt ccctgagagt gctgctggtc atcctgtggc tgcagctgtc ttgggtctgg    60
tcccagcaga agaagtggaa acaggaccct ggacctctga gcgttccaga aggcgccatc   120
gtcagcctga attgcaccta cagcaacagc gccttccagt acttcatgtg gtacagacag   180
tactcccgga agggccccga gctgctgatg tacacataca gcagcggcaa caagaggac   240 ggccggttta cagcccaggt ggacaagagc agcaagtaca tctccctgtt catccgggac   300
agccagccta gcgatagcgc cacatacctg tgcgccatgt ctggcacagg cggcttcaag   360
accatcttcg gagccggcac acggctgttc gtgaaggcca ac                      402

<210> SEQ ID NO 110
<211> LENGTH: 408
<212> TYPE: DNA

<213> ORGANISM: Artificial Sequence
<220> FEATURE:
<223> OTHER INFORMATION: beta chain variable region of TCR2705 - codon optimized

<400> SEQUENCE: 110

```
atgggatgta gactgctgtg ttgtgccgtg ctgtgtctgc ttggagctgg cgaactggtg      60
cctatggaaa ccggcgtgac ccagacacct agacacctgg tcatgggcat gacaaacaag     120
aaaagcctga gtgcgagca gcacctgggc acaatgcca tgtactgta caagcagagc        180
gccaagaaac ccctggaact gatgttcgtg tacagcctgg aagagagggt cgagaacaac     240
agcgtgccca gcagattcag ccctgagtgc cctaatagca gccacctgtt tctgcatctg     300
cacaccctgc agcctgagga ctctgccctg tatctgtgtg ccagcagcca ggacagaccc     360
aactactacg gctacacctt tggcagcggc accagactga ccgtggtg                  408
```

<210> SEQ ID NO 111
<211> LENGTH: 7
<212> TYPE: PRT
<213> ORGANISM: Homo sapiens

<400> SEQUENCE: 111

Thr Ile Ser Gly Thr Asp Tyr
1               5

<210> SEQ ID NO 112
<211> LENGTH: 5
<212> TYPE: PRT
<213> ORGANISM: Homo sapiens

<400> SEQUENCE: 112

Gly Leu Thr Ser Asn
1               5

<210> SEQ ID NO 113
<211> LENGTH: 16
<212> TYPE: PRT
<213> ORGANISM: Homo sapiens

<400> SEQUENCE: 113

Cys Ile Leu Arg Asp Arg Tyr Gly Gly Ser Gln Gly Asn Leu Ile Phe
1               5                   10                  15

<210> SEQ ID NO 114
<211> LENGTH: 5
<212> TYPE: PRT
<213> ORGANISM: Homo sapiens

<400> SEQUENCE: 114

Met Asn His Glu Tyr
1               5

<210> SEQ ID NO 115
<211> LENGTH: 6
<212> TYPE: PRT
<213> ORGANISM: Homo sapiens

<400> SEQUENCE: 115

Ser Val Gly Glu Gly Thr
1               5

<210> SEQ ID NO 116
<211> LENGTH: 18

```
<212> TYPE: PRT
<213> ORGANISM: Homo sapiens

<400> SEQUENCE: 116

Cys Ala Ser Ser Tyr Trp Pro Thr Thr Gly Glu Ser Thr Asp Thr Gln
1               5                   10                  15

Tyr Phe

<210> SEQ ID NO 117
<211> LENGTH: 131
<212> TYPE: PRT
<213> ORGANISM: Homo sapiens

<400> SEQUENCE: 117

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
                20                  25                  30

Glu Pro Val His Leu Pro Cys Asn His Ser Thr Ile Ser Gly Thr Asp
            35                  40                  45

Tyr Ile His Trp Tyr Arg Gln Leu Pro Ser Gln Gly Pro Glu Tyr Val
        50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
                85                  90                  95

Leu Arg Asp Ala Ala Val Tyr Tyr Cys Ile Leu Arg Asp Arg Tyr Gly
            100                 105                 110

Gly Ser Gln Gly Asn Leu Ile Phe Gly Lys Gly Thr Lys Leu Ser Val
        115                 120                 125

Lys Pro Asn
        130

<210> SEQ ID NO 118
<211> LENGTH: 136
<212> TYPE: PRT
<213> ORGANISM: Homo sapiens

<400> SEQUENCE: 118

Met Ser Leu Gly Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
                20                  25                  30

Lys Thr Gly Gln Ser Met Thr Leu Leu Cys Ala Gln Asp Met Asn His
            35                  40                  45

Glu Tyr Met Tyr Trp Tyr Arg Gln Asp Pro Gly Met Gly Leu Arg Leu
        50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
            100                 105                 110

Ser Tyr Trp Pro Thr Thr Gly Glu Ser Thr Asp Thr Gln Tyr Phe Gly
        115                 120                 125

Pro Gly Thr Arg Leu Thr Val Leu
        130                 135
```

<210> SEQ ID NO 119
<211> LENGTH: 393
<212> TYPE: DNA
<213> ORGANISM: Artificial Sequence
<220> FEATURE:
<223> OTHER INFORMATION: alpha chain variable region of TCR2709 - codon
      optimized

<400> SEQUENCE: 119

```
atgaagctgg tcaccagcat acagtgctg ctgagcctgg gaattatggg cgacgccaag    60
accacacagc ccaacagcat ggaaagcaac gaagaggaac ccgtgcatct gccctgcaac   120
cacagcacaa tcagcggcac cgactacatc cactggtata gacagctgcc ctctcagggc   180
cccgagtatg tgattcacgg actgaccagc aacgtgaaca accggatggc ctctctggcc   240
attgccgagg acagaaagag cagcaccctg atcctgcaca gagccacact gagagatgcc   300
gccgtgtact actgcatcct gcgggataga tacggcggca gccagggcaa tctgatcttt   360
ggcaagggca ccaagctgag cgtgaagccc aac                                393
```

<210> SEQ ID NO 120
<211> LENGTH: 408
<212> TYPE: DNA
<213> ORGANISM: Artificial Sequence
<220> FEATURE:
<223> OTHER INFORMATION: beta chain variable region of TCR2709 - codon
      optimized

<400> SEQUENCE: 120

```
atgtctcttg gattgctttg ctgcggcgcc ttcagcctgc tttgggctgg acctgttaat    60
gccggcgtga cccagacacc taagttccgg gtgctgaaaa ccggccagag catgacactg   120
ctgtgcgccc aggacatgaa ccacgagtac atgtattggt acagacagga ccccggcatg   180
ggcctgagac tgatccacta ttctgtcggc gagggcacca cagccaaagg cgaagttcct   240
gacggctaca cgtgtcccg gctgaagaag cagaacttcc tgctgggcct cgagtctgcc   300
gctccatctc agaccagcgt gtacttctgt gccagcagct actggcctac caccggcgag   360
tctaccgaca cacagtattt cggccctggc accagactga ccgtgctg               408
```

<210> SEQ ID NO 121
<211> LENGTH: 7
<212> TYPE: PRT
<213> ORGANISM: Homo sapiens

<400> SEQUENCE: 121

Thr Ser Glu Asn Asn Tyr Tyr
1               5

<210> SEQ ID NO 122
<211> LENGTH: 8
<212> TYPE: PRT
<213> ORGANISM: Homo sapiens

<400> SEQUENCE: 122

Gln Glu Ala Tyr Lys Gln Gln Asn
1               5

<210> SEQ ID NO 123
<211> LENGTH: 17
<212> TYPE: PRT
<213> ORGANISM: Homo sapiens

<400> SEQUENCE: 123

Cys Ala Phe Met Lys Pro Tyr Ser Gly Gly Gly Ala Asp Gly Leu Thr
1               5                   10                  15

Phe

<210> SEQ ID NO 124
<211> LENGTH: 5
<212> TYPE: PRT
<213> ORGANISM: Homo sapiens

<400> SEQUENCE: 124

Pro Arg His Asp Thr
1               5

<210> SEQ ID NO 125
<211> LENGTH: 6
<212> TYPE: PRT
<213> ORGANISM: Homo sapiens

<400> SEQUENCE: 125

Phe Tyr Glu Lys Met Gln
1               5

<210> SEQ ID NO 126
<211> LENGTH: 16
<212> TYPE: PRT
<213> ORGANISM: Homo sapiens

<400> SEQUENCE: 126

Cys Ala Ser Ser Leu Ala Gly Thr Thr Val Tyr Asn Glu Gln Phe Phe
1               5                   10                  15

<210> SEQ ID NO 127
<211> LENGTH: 139
<212> TYPE: PRT
<213> ORGANISM: Homo sapiens

<400> SEQUENCE: 127

Met Thr Arg Val Ser Leu Leu Trp Ala Val Val Val Ser Thr Cys Leu
1               5                   10                  15

Glu Ser Gly Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Asn Asn Tyr Tyr Leu Phe Trp Tyr Lys Gln Pro Pro Ser Arg Gln
        50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Phe Met Lys Pro Tyr Ser Gly Gly Gly Ala Asp Gly Leu Thr Phe
        115                 120                 125

Gly Lys Gly Thr His Leu Ile Ile Gln Pro Tyr
    130                 135

<210> SEQ ID NO 128
<211> LENGTH: 144
<212> TYPE: PRT

<213> ORGANISM: Homo sapiens

<400> SEQUENCE: 128

```
Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Ala Gly Thr Thr
        115                 120                 125

Val Tyr Asn Glu Gln Phe Phe Gly Pro Gly Thr Arg Leu Thr Val Leu
    130                 135                 140
```

<210> SEQ ID NO 129
<211> LENGTH: 417
<212> TYPE: DNA
<213> ORGANISM: Artificial Sequence
<220> FEATURE:
<223> OTHER INFORMATION: alpha chain variable region of TCR2716 - codon optimized

<400> SEQUENCE: 129

```
atgaccagag tgtctctgct gtgggccgtc gtggtgtcca catgtctgga atctggcatg     60
gcccagacag tgacccagag ccagcctgag atgtctgtgc aagaggccga gactgtgacc    120
ctgtcctgca cctacgatac cagcgagaac aactactacc tgttctggta caagcagcct    180
cctagccggc agatgatcct ggtcatcaga caagaggcct ataagcagca gaacgccacc    240
gagaacagat tcagcgtgaa cttccagaag gccgccaaga gcttcagcct gaagatcagc    300
gatagccagc tgggagacac cgccatgtat ttctgcgcct ttatgaagcc ctacagcggc    360
ggaggtgccg atggcctgac atttggaaag ggcacccacc tgattatcca gccgtac      417
```

<210> SEQ ID NO 130
<211> LENGTH: 432
<212> TYPE: DNA
<213> ORGANISM: Artificial Sequence
<220> FEATURE:
<223> OTHER INFORMATION: beta chain variable region of TCR2716 - codon optimized

<400> SEQUENCE: 130

```
atgctttctc cagatctgcc tgacagcgcc tggaacacca gactgctgtg tcacgtgatg     60
ctgtgtctgc tgggagccgt gtctgttgcc gctggcgtta ccagtctcc tcggcacctg    120
atcaaagaga gagagagac agccacactg aagtgctacc ccattccacg gcacgacacc    180
gtgtactggt atcagcaagg cccaggccag gatcctcagt tcctgatcag cttctacgag    240
aagatgcaga gcgacaaggg cagcatcccc gacagatttt ctgcccagca gttcagcgac    300
taccacagcg agctgaacat gagcagcctg gaactgggcg atagcgccct gtacttttgt    360
```

```
gcctcttctc tggccggcac cacagtgtac aacgagcagt ttttcggccc tggcaccagg    420
ctgaccgtgc tg                                                         432
```

<210> SEQ ID NO 131
<211> LENGTH: 7
<212> TYPE: PRT
<213> ORGANISM: Homo sapiens

<400> SEQUENCE: 131

Asn Ile Ala Thr Asn Asp Tyr
1               5

<210> SEQ ID NO 132
<211> LENGTH: 5
<212> TYPE: PRT
<213> ORGANISM: Homo sapiens

<400> SEQUENCE: 132

Gly Tyr Lys Thr Lys
1               5

<210> SEQ ID NO 133
<211> LENGTH: 13
<212> TYPE: PRT
<213> ORGANISM: Homo sapiens

<400> SEQUENCE: 133

Cys Leu Val Gly Ala Asp Ser Asn Tyr Gln Leu Ile Trp
1               5                   10

<210> SEQ ID NO 134
<211> LENGTH: 5
<212> TYPE: PRT
<213> ORGANISM: Homo sapiens

<400> SEQUENCE: 134

Ser Gly Asp Leu Ser
1               5

<210> SEQ ID NO 135
<211> LENGTH: 6
<212> TYPE: PRT
<213> ORGANISM: Homo sapiens

<400> SEQUENCE: 135

Tyr Tyr Asn Gly Glu Glu
1               5

<210> SEQ ID NO 136
<211> LENGTH: 14
<212> TYPE: PRT
<213> ORGANISM: Homo sapiens

<400> SEQUENCE: 136

Cys Ala Ser Ser Pro Gly Gly Gly Ala Tyr Glu Gln Tyr Phe
1               5                   10

<210> SEQ ID NO 137
<211> LENGTH: 128
<212> TYPE: PRT
<213> ORGANISM: Homo sapiens

<400> SEQUENCE: 137

Met Arg Gln Val Ala Arg Val Ile Val Phe Leu Thr Leu Ser Thr Leu

```
                1               5                  10                  15
Ser Leu Ala Lys Thr Thr Gln Pro Ile Ser Met Asp Ser Tyr Glu Gly
                20                  25                  30

Gln Glu Val Asn Ile Thr Cys Ser His Asn Asn Ile Ala Thr Asn Asp
                35                  40                  45

Tyr Ile Thr Trp Tyr Gln Gln Phe Pro Ser Gln Gly Pro Arg Phe Ile
        50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Gly Ala Asp Ser Asn
                100                 105                 110

Tyr Gln Leu Ile Trp Gly Ala Gly Thr Lys Leu Ile Ile Lys Pro Asp
            115                 120                 125
```

<210> SEQ ID NO 138
<211> LENGTH: 132
<212> TYPE: PRT
<213> ORGANISM: Homo sapiens

<400> SEQUENCE: 138

```
Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
                20                  25                  30

Ala Thr Gly Gln Arg Val Thr Leu Arg Cys Ser Pro Arg Ser Gly Asp
                35                  40                  45

Leu Ser Val Tyr Trp Tyr Gln Gln Ser Leu Asp Gln Gly Leu Gln Phe
        50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
                100                 105                 110

Ser Pro Gly Gly Gly Ala Tyr Glu Gln Tyr Phe Gly Pro Gly Thr Arg
            115                 120                 125

Leu Thr Val Thr
        130
```

<210> SEQ ID NO 139
<211> LENGTH: 384
<212> TYPE: DNA
<213> ORGANISM: Artificial Sequence
<220> FEATURE:
<223> OTHER INFORMATION: alpha chain variable region of TCR2719 - codon
      optimized

<400> SEQUENCE: 139

```
atgagacagg tggccagagt gatcgtgttc ctgacactga gcaccctgag cctggccaag    60
accacacagc ccatcagcat ggacagctac gagggccaag aagtgaacat cacctgtagc   120
cacaacaata tcgccaccaa cgactacatc acgtggtatc aacagttccc cagtcaaggc   180
cctcggttca tcatccaagg ctacaagacc aaagtgacca acgaggtggc ctctctgttc   240
atccccgccg acagaaagag cagcaccctg tctctgccta gagtgtccct gagcgatacc   300
```

```
gccgtgtact actgtctcgt gggcgccgac tctaactacc agctgatttg gggagccggc      360
accaagctga tcatcaagcc cgac                                             384
```

<210> SEQ ID NO 140
<211> LENGTH: 396
<212> TYPE: DNA
<213> ORGANISM: Artificial Sequence
<220> FEATURE:
<223> OTHER INFORMATION: beta chain variable region of TCR2719 - codon
      optimized

<400> SEQUENCE: 140

```
atgggtttta gactgctgtg ctgcgtggcc ttctgtctgc ttggagctgg ccctgtggat      60
agcggcgtta cccagacacc taagcacctg atcacagcca caggccagcg cgtgaccctg     120
agatgttctc ctagaagcgg cgacctgagc gtgtactggt atcagcagtc tctggaccag     180
ggcctgcagt tcctgatcca gtactacaac ggcgaggaaa gagccaaggg caacatcctg     240
gaacggttca gcgcccagca gttcccagat ctgcacagcg agctgaacct gagcagcctg     300
gaactgggag atagcgccct gtacttctgc gccagttctc ctggtggcgg agcctacgag     360
cagtattttg gccctggcac cagactgacc gtgacc                               396
```

<210> SEQ ID NO 141
<211> LENGTH: 10
<212> TYPE: PRT
<213> ORGANISM: Homo sapiens

<400> SEQUENCE: 141

Leu Pro Ile His Ile Thr Tyr Ala Ala Met
1               5                   10

<210> SEQ ID NO 142
<211> LENGTH: 10
<212> TYPE: PRT
<213> ORGANISM: Homo sapiens

<400> SEQUENCE: 142

Arg Pro Arg Met Ile Gly Tyr Gly Ala Ile
1               5                   10

<210> SEQ ID NO 143
<211> LENGTH: 10
<212> TYPE: PRT
<213> ORGANISM: Homo sapiens

<400> SEQUENCE: 143

Arg Pro Ala Met Ile Pro Tyr Trp Ala Leu
1               5                   10

<210> SEQ ID NO 144
<211> LENGTH: 10
<212> TYPE: PRT
<213> ORGANISM: Homo sapiens

<400> SEQUENCE: 144

Val Pro Ile Ile Ile Lys Tyr Leu Met Phe
1               5                   10

<210> SEQ ID NO 145
<211> LENGTH: 10
<212> TYPE: PRT
<213> ORGANISM: Homo sapiens

```
<400> SEQUENCE: 145

Arg Pro Val Pro Ile Ser Tyr His Gln Leu
1               5                   10

<210> SEQ ID NO 146
<211> LENGTH: 10
<212> TYPE: PRT
<213> ORGANISM: Homo sapiens

<400> SEQUENCE: 146

Lys Pro Ile Arg Ile Gly Tyr Lys Ile Trp
1               5                   10

<210> SEQ ID NO 147
<211> LENGTH: 10
<212> TYPE: PRT
<213> ORGANISM: Homo sapiens

<400> SEQUENCE: 147

Arg Pro Asp Leu Ile Asp Tyr Lys Ser Leu
1               5                   10

<210> SEQ ID NO 148
<211> LENGTH: 10
<212> TYPE: PRT
<213> ORGANISM: Homo sapiens

<400> SEQUENCE: 148

Leu Pro Leu Tyr Ile Ser Tyr Val Ala Met
1               5                   10

<210> SEQ ID NO 149
<211> LENGTH: 10
<212> TYPE: PRT
<213> ORGANISM: Homo sapiens

<400> SEQUENCE: 149

Leu Pro Thr Arg Ile Ala Tyr Tyr Ala Met
1               5                   10

<210> SEQ ID NO 150
<211> LENGTH: 10
<212> TYPE: PRT
<213> ORGANISM: Homo sapiens

<400> SEQUENCE: 150

Thr Pro Pro Lys Ile Pro Tyr Lys Ala Ile
1               5                   10

<210> SEQ ID NO 151
<211> LENGTH: 10
<212> TYPE: PRT
<213> ORGANISM: Homo sapiens

<400> SEQUENCE: 151

Leu Pro Gln Ser Ile Val Tyr Lys Tyr Met
1               5                   10
```

```
<210> SEQ ID NO 152
<211> LENGTH: 10
<212> TYPE: PRT
<213> ORGANISM: Homo sapiens

<400> SEQUENCE: 152

Arg Pro Gln Pro Ile Tyr Tyr Gly Phe Ser
1               5                   10
```

The invention claimed is:

1. A nucleic acid encoding a TCR alpha chain construct comprising a CDR1 sequence having SEQ ID NO: 91, a CDR2 sequence having SEQ ID NO: 92, and a CDR3 sequence having SEQ ID NO: 93; and a nucleic acid encoding a TCR beta chain construct comprising a CDR1 sequence having SEQ ID NO:94, a CDR2 sequence having SEQ ID NO: 95 and a CDR3 sequence having SEQ ID NO: 96; wherein the TCR alpha chain construct and the TCR beta chain construct are encoded on the same or different nucleic acids; and wherein the TCR alpha chain construct and TCR beta chain construct form a TCR construct that is capable of specifically binding to a MYD88 L265P peptide of SEQ ID NO: 2 in the context of HLA-B*07:02.

2. The nucleic acid or nucleic acids of claim 1, wherein the TCR alpha chain construct comprises a variable region having a sequence identity of at least 90% to SEQ ID NO: 97, and/or wherein the TCR beta chain construct comprises a variable region having a sequence identity of at least 90% to SEQ ID NO: 98.

3. The nucleic acid or nucleic acids of claim 1, encoding the TCR alpha chain construct and the TCR beta chain construct, wherein the TCR encoded by the construct has an avidity with KD value of $7.4\times10^{-9}$ M or lower to the peptide of SEQ ID NO: 2 in the context of HLA-B*07:02.

4. The nucleic acid or nucleic acids of claim 3, wherein the $K_D$ value is $2.4\times10^{-9}$ M or lower.

5. The nucleic acid or nucleic acids of claim 1, wherein the TCR alpha chain construct and/or the TCR beta chain construct further comprise a constant region selected from the group comprising a human constant region, a murine constant region or a chimeric constant region.

6. The nucleic acid or nucleic acids of claim 1, encoding the TCR alpha and beta chain construct of the TCR construct, wherein the nucleic acid is selected from the group comprising a viral vector, a transposon or a vector suitable for CRISPR/CAS based recombination.

7. A host cell comprising the nucleic acid or nucleic acids of claim 1.

8. The host cell of claim 7, wherein the host cell is a human CD8+ T cell.

9. A pharmaceutical composition comprising
a) a nucleic acid or nucleic acids of claim 1 encoding a TCR construct capable of specifically binding to a MYD88 L265P peptide of SEQ ID NO: 2 in the context of HLA-B*07:02; or
b) a protein encoded by said nucleic acid or nucleic acids; or
c) a host cell comprising said nucleic acid or protein and expressing a TCR construct capable of specifically binding to a MYD88 L265P peptide comprising SEQ ID NO: 2 in the context of HLAB*07:02.

10. A method of treating non-Hodgkin B-cell lymphoma in a patient suspected of comprising cells expressing a MYD88 L265P protein comprising administering an effective amount of the pharmaceutical composition of claim 9 to said patient.

11. The method of claim 10, wherein the method is for immune therapy selected from the group consisting of adoptive T cell therapy or TCR gene therapy of the patient comprising cells expressing the MYD88 L265P protein.

12. The method of claim 10, wherein the patient has a non-Hodgkin B-cell lymphoma selected from the group consisting of:
diffuse large B-cell lymphoma (DLBCL);
lymphoplasmacytic lymphoma (LPL); and
IgM monoclonal gammopathy (IgM MGUS).

13. The method of claim 12, wherein the patient has activated B-cell-type DLBCL (ABC-DLBCL), or Primary CNS lymphoma, cutaneous DLBCL, leg-type DLBCL, or testicular DLBCL.

14. The method of claim 12, wherein the patient has Waldenstrom macroglobulinemia (WM).

15. A protein comprising a TCR alpha chain construct and TCR beta chain construct encoded by the nucleic acid or the nucleic acids of claim 1.

16. A host cell comprising the protein of claim 15.

17. The host cell of claim 16, wherein the host cell is a human CD8+ T cell.

* * * * *